(12) United States Patent
Chirica et al.

(10) Patent No.: US 8,346,574 B2
(45) Date of Patent: Jan. 1, 2013

(54) SYSTEMS AND METHODS FOR TRACKING AND PROVIDING WORKFLOW INFORMATION

(75) Inventors: Laura Chirica, Bunkeflostrand (SE); Mats Grahn, Ystad (SE); Stephen Jones, Wigan (GB)

(73) Assignee: DAKO Denmark A/S (DK)

( * ) Notice: Subject to any disclaimer, the term of this patent is extended or adjusted under 35 U.S.C. 154(b) by 263 days.

(21) Appl. No.: 12/394,324

(22) Filed: Feb. 27, 2009

(65) Prior Publication Data

US 2009/0222746 A1    Sep. 3, 2009

Related U.S. Application Data

(60) Provisional application No. 61/064,359, filed on Feb. 29, 2008, provisional application No. 61/071,852, filed on May 21, 2008.

(51) Int. Cl.
*G06Q 50/00*    (2006.01)
(52) U.S. Cl. .................................. 705/3; 705/2
(58) Field of Classification Search ................. 702/108; 705/2, 3, 10; 434/276, 350
See application file for complete search history.

(56) References Cited

U.S. PATENT DOCUMENTS

| | | | |
|---|---|---|---|
| 5,366,896 A | 11/1994 | Margrey et al. | |
| 6,783,367 B1 * | 8/2004 | Wang et al. | 434/276 |
| 6,813,473 B1 * | 11/2004 | Bruker | 434/350 |
| 7,016,949 B1 * | 3/2006 | Tagawa | 709/223 |
| 7,747,406 B2 * | 6/2010 | Boing et al. | 702/108 |
| 7,877,270 B2 * | 1/2011 | Sitomer et al. | 705/2 |
| 2004/0135804 A1 * | 7/2004 | Pellaz et al. | 345/734 |
| 2004/0189718 A1 | 9/2004 | Stein et al. | |
| 2006/0031095 A1 * | 2/2006 | Barth et al. | 705/2 |
| 2006/0031112 A1 * | 2/2006 | Barth et al. | 705/10 |
| 2007/0282997 A1 * | 12/2007 | Trochman | 709/224 |
| 2008/0109759 A1 * | 5/2008 | Stambaugh | 715/835 |
| 2008/0235055 A1 * | 9/2008 | Mattingly et al. | 705/3 |
| 2009/0259321 A1 * | 10/2009 | Stellari et al. | 700/9 |

FOREIGN PATENT DOCUMENTS

WO    WO 2007/021747 A2    2/2007

OTHER PUBLICATIONS

International Search Report from PCT/DK2009/000055 mailed on May 8, 2009 (2 pages).

* cited by examiner

*Primary Examiner* — Gerald J. O'Connor
*Assistant Examiner* — Jonathan K Ng
(74) *Attorney, Agent, or Firm* — Finnegan, Henderson, Farabow, Garrett & Dunner, LLP.

(57) ABSTRACT

A tangible computer-readable storage device storing computer-executable program instructions that generate a user interface for displaying workflow information associated with a tissue specimen in a pathology laboratory. The program instructions may be configured to perform a method including displaying a virtual laboratory component representing a physical pathology laboratory having one or more laboratory stations for processing the tissue specimen, wherein the tissue specimen is processed by the one or more laboratory stations according to a workflow, and displaying a specimen indicator that indicates a current specimen state based on a current relationship of the tissue specimen to the workflow. The method may further include enabling a first active component associated with the virtual laboratory component, wherein the first active component is configured to receive a user selection of a laboratory station and generating a supplemental view component of the selected laboratory station in response to the user selection, wherein the supplemental view provides supplemental information on processing by the selected laboratory station of the tissue specimen.

35 Claims, 29 Drawing Sheets

Workflow Visualization

Data Analysis and Reporting

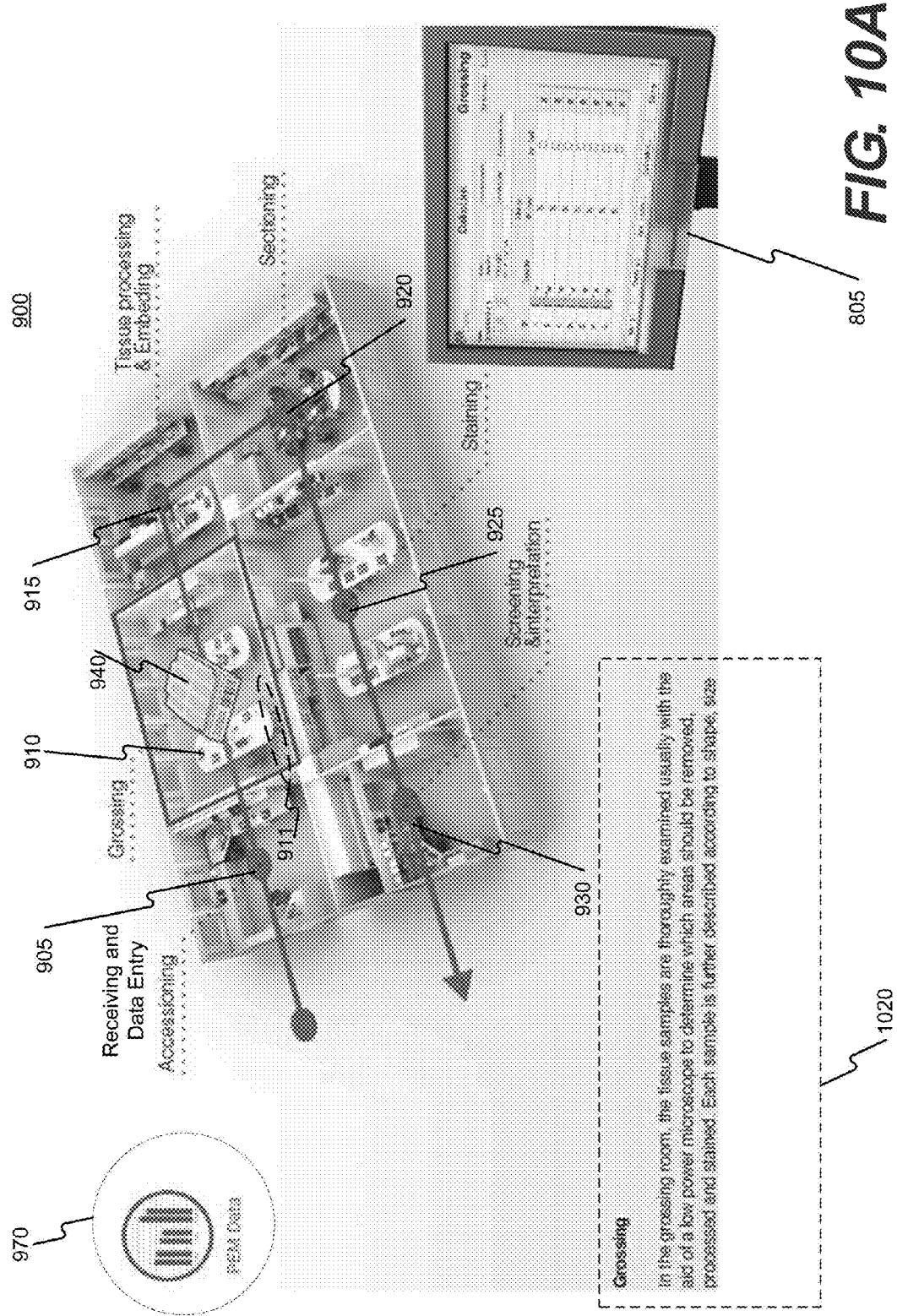

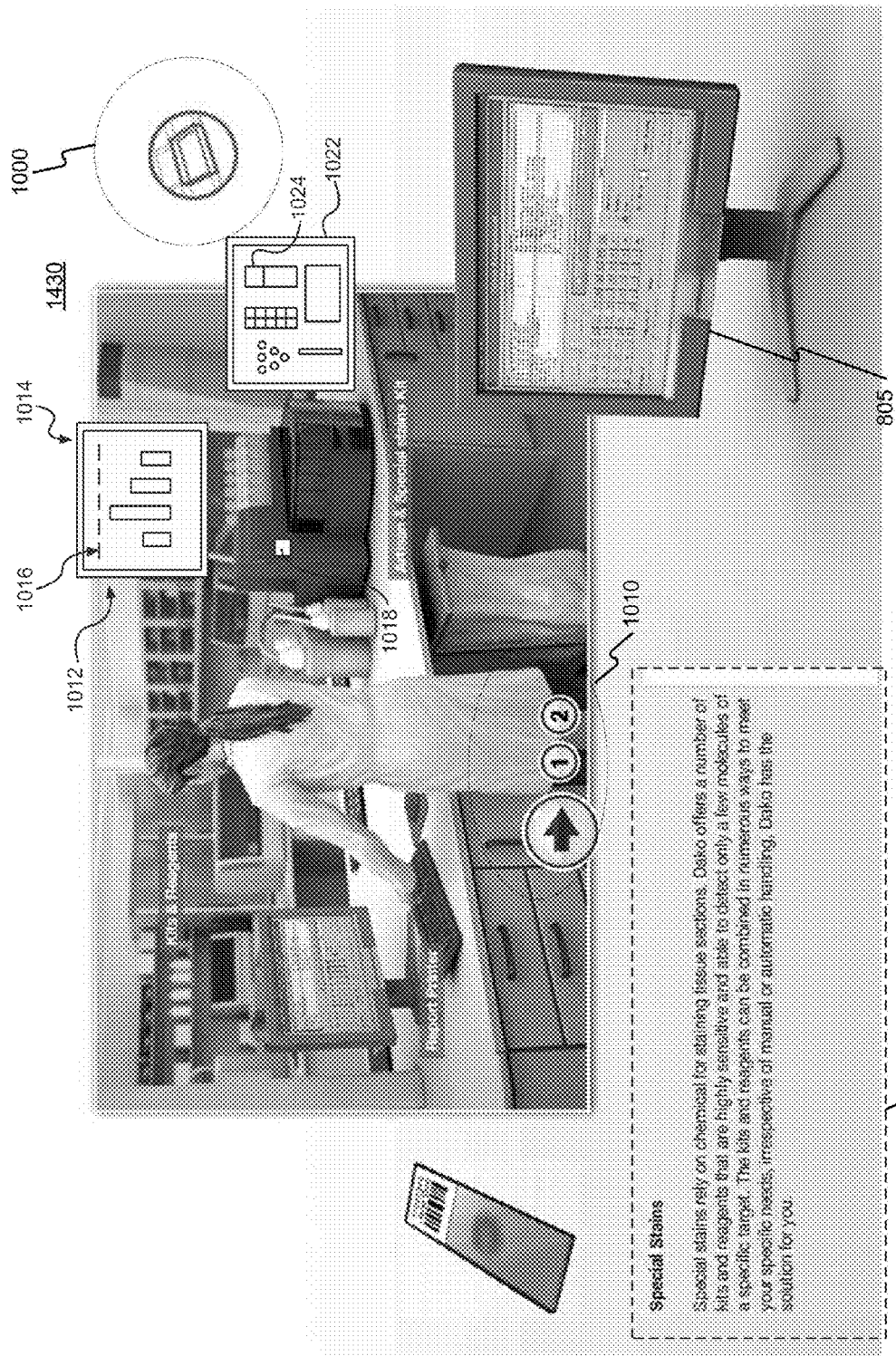

SYSTEMS AND METHODS FOR TRACKING AND PROVIDING WORKFLOW INFORMATION

RELATED APPLICATIONS

This application is based upon and claims the benefit of priority from U.S. Provisional Application Nos. 61/064,359 filed on Feb. 29, 2008, and 61/071,852 filed on May 21, 2008, the entire contents of which are incorporated herein by reference.

FIELD OF THE INVENTION

The present disclosure relates to laboratory data and, more particularly, to tracking and providing workflow data associated with a laboratory to a user.

BACKGROUND OF THE INVENTION

Advances in analytical science have made it possible to extract a wide variety of information from a biological specimen. For example, it may be possible to assess the health, identify possible future health issues, and provide information related to the genetic makeup of an individual from which the specimen was obtained. The benefits of such analysis, however, may be lost if results are associated with the wrong individual and/or if the specimen is processed incorrectly.

Many of these biological specimens may be processed in laboratories. The laboratory may receive such specimens from institutions, including, for example, hospitals, clinics, and/or the police, and also, to a lesser extent, from individuals themselves. These specimens may include, for example, tissue removed during a surgical procedure, tissue from crime scenes, and test materials from a home testing kit (e.g., an HIV test), among other things.

In a laboratory, many resources and man-hours may be consumed to process, prepare, and test a specimen. Each specimen may also pass through many lab stations and may be handled by many operators, leading to potential losses in efficiency and clerical errors, among other things. For example, a laboratory may use an accessioning station to receive and prep the specimen (e.g., by labeling the specimen, listing the requested tests, etc.) before further analysis. After accessioning, a technician may carry a specimen to a grossing station to measure, cut, and record a description of the specimen. The specimen may then be manually altered (e.g., by embedding, sectioning, staining, imaging, etc.) at subsequent stations where process data may or may not be tracked. Throughout execution of these processes, multiple technicians may handle the specimen and record data associated with it. Each station or process thus introduces more costs and opportunities for error. For example, one or more technicians may repeatedly perform process steps incorrectly (e.g., use an incorrect stain, embed a sample in too much paraffin, section a specimen too closely, etc.). Because such processes may not be tracked, and/or because such data may not be easily and succinctly summarized for review by administrators, costly errors may go uncorrected.

To help avoid errors during the lab processing, laboratories may employ elaborate systems of paperwork. However, this incurs yet additional expenses. Many laboratories use log books, tracking sheets, and other manual processes to help identify and track specimens. However, these manual methods do not adequately provide information on the workflow of a specimen as it is processed in the laboratory. Nor do manual methods lend themselves to quickly and efficiently providing high-level summary data to the lab manager or others with an interest in gaining an understanding of the overall operations of the laboratory. There thus exists a need to track and provide workflow information associated with a specimen as it is processed in a laboratory and to present the information in meaningful ways at both detailed and macro levels.

SUMMARY OF THE INVENTION

According to some aspects the present disclosure provides a tangible computer-readable storage device storing computer-executable program instructions that generate a user interface for displaying workflow information associated with a tissue specimen in a pathology laboratory.

The program instructions may be configured to perform a method including displaying a virtual laboratory component representing a physical pathology laboratory having one or more laboratory stations for processing the tissue specimen, wherein the tissue specimen is processed by the one or more laboratory stations according to a workflow, and displaying a specimen indicator that indicates a current specimen state based on a current relationship of the tissue specimen to the workflow. The method may further include enabling a first active component associated with the virtual laboratory component, wherein the first active component is configured to receive a user selection of a laboratory station and generating a supplemental view component of the selected laboratory station in response to the user selection, wherein the supplemental view provides supplemental information on processing by the selected laboratory station of the tissue specimen According to another aspect, the present disclosure provides a computer-implemented method for generating a user interface to display workflow information associated with a specimen in a laboratory.

The method may include displaying a virtual laboratory component representing a physical laboratory having one or more virtual laboratory stations, enabling a first active component associated with the virtual laboratory component, wherein the first active component is configured to receive a user selection of a virtual laboratory station included in the virtual laboratory component, and generating a supplemental view component of the selected laboratory station in response to the user selection.

According to yet another aspect, the present disclosure provides a user interface, generated by a computer, for displaying workflow information associated with a specimen in a laboratory. The interface may include a virtual laboratory component representing a physical laboratory having one or more virtual laboratory stations, a first active component associated with the virtual laboratory component, wherein the first active component is configured to receive a user selection of a virtual laboratory station included in the virtual laboratory component, and a supplemental view component of the selected laboratory station, wherein the supplemental view component is displayed in response to the user selection.

According to yet another aspect, the present disclosure provides a method for providing workflow information associated with processing of specimens in a physical laboratory. The method may include storing device data associated with a laboratory device in the physical laboratory, displaying a virtual laboratory component representing the physical laboratory having one or more laboratory stations, and enabling a first active component associated with the virtual laboratory component, wherein the first active component is configured to receive a user request for workflow information associated with a selected laboratory station. The method may further include processing, based on the request, the device data to generate the workflow information and providing the workflow information to the user.

According to yet another aspect, the present disclosure provides a system for providing data related to a physical laboratory. The system may include a workflow server configured to receive data related to a physical laboratory, a laboratory device in communication with the workflow server and configured to provide the data, a display device; and an interface component. The interface component may be configured to display a virtual laboratory component representing the physical laboratory having one or more laboratory stations enable a first active component associated with the virtual laboratory component, wherein the first active component is configured to receive a user request for workflow information associated with a selected laboratory station, process, based on the request, the device data to generate the workflow information, and provide the workflow information to the user.

It is to be understood that both the foregoing general description and the following detailed description are exemplary and explanatory only and are not restrictive of the invention, as described and claimed. Further features and/or variations may be provided in addition to those set forth herein. For example, the present invention may be directed to various combinations and subcombinations of the disclosed features and/or combinations and subcombinations of several further features disclosed below in the detailed description.

BRIEF DESCRIPTION OF THE DRAWINGS

The accompanying drawings, which are incorporated in and constitute a part of this specification, show certain aspects of the present invention and, together with the description, help explain some of the principles associated with the invention. In the drawings:

FIG. 10A is an exemplary depiction of a virtual laboratory following a user selection of a virtual grossing station;

FIG. 13C is an exemplary representation of an interface providing a supplemental component associated with a drilled down view of a virtual staining station;

DESCRIPTION OF THE EMBODIMENTS

Reference will now be made in detail to the invention, examples of which are illustrated in the accompanying drawings. The implementations set forth in the following description do not represent all implementations consistent with the claimed invention. Instead, they are merely some examples consistent with certain aspects related to the invention. Wherever possible, the same reference numbers will be used throughout the drawings to refer to the same or like parts.

Systems and methods consistent with the invention may track and provide workflow information associated with a specimen in a laboratory. As used herein, the term "specimen" broadly refers to any material or piece of material obtained for the purpose of performing an operation in a laboratory. For example, the laboratory operation may involve preparation of the specimen, analysis or testing of the specimen, or storage of the specimen. Exemplary types of specimens include tissue or other biologic samples taken from an animal or human. Further, as used herein, the term "workflow" broadly refers to a path or order of operations that a specimen may follow in a laboratory. For example, the term workflow may reflect the order in which a series of laboratory stations may process the specimen. The term "workflow information" may broadly refer to any information and/or data related to a specimen's workflow.

In one exemplary implementation, systems and methods consistent with the invention may provide a computer-implemented user interface for displaying a workflow or workflow information associated with a specimen in a laboratory. For example, the workflow user interface may display a virtual laboratory representing the actual or physical laboratory or laboratories that process the specimen. Through the virtual laboratory representation, the user interface may further illustrate a workflow for the specimen as it is processed in the laboratory. As described in more detail below, exemplary embodiments further include a specimen type indicator to illustrate the current specimen state as the specimen is processed in the laboratory according to the workflow.

Systems and methods consistent with the present disclosure thus allow laboratory administrators and other hospital staff to easily visualize a workflow associated with a specimen in a physical laboratory. Further, systems consistent with the invention may also provide data related to the laboratory's processing of specimens through the workflow interface. For example, the workflow user interface may provide a framework for viewing high level data associated with the workflow. As described in more detail below, this data may include specimen specific data as well as laboratory data.

Figure 1:
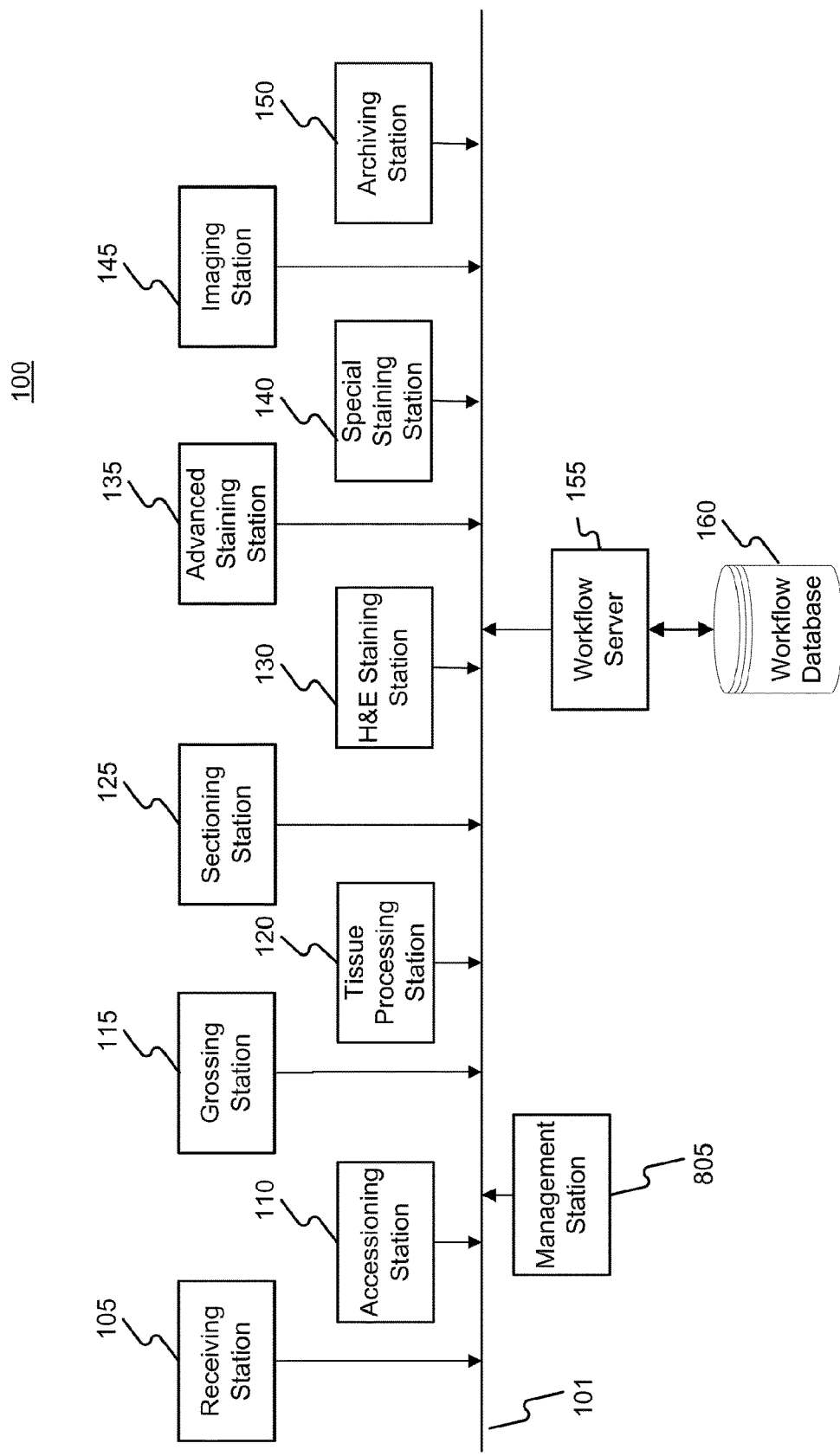
FIG. 1 is a block diagram representing an exemplary physical laboratory configuration according to some embodiments of the present disclosure.

FIG. 1 is a block diagram of an exemplary physical laboratory environment 100 consistent with exemplary embodiments of the present disclosure. The exemplary configuration shown in FIG. 1 generally relates to a pathology laboratory. However, systems and methods consistent with the invention equally apply to other types of laboratories. Thus, as used herein, the term "physical laboratory" broadly refers to any type of actual laboratory (or laboratories) for handling specimens. The term "virtual laboratory," as used herein, broadly refers to a virtual illustration or depiction of a physical laboratory or laboratories. For example, a virtual laboratory may be a computer-implemented graphical representation or model of a physical laboratory. The virtual laboratory may depict the appearance or organization of the physical laboratory, or may include logical components substantially similar to the physical laboratory.

As shown in FIG. 1, laboratory environment 100 may include a network 101, a receiving station 105, an accessioning station 110, a grossing station 115, a tissue processing and embedding station 120, a sectioning station 125, an H&E staining station 130, an advanced staining station 135, a special staining station 140, an imaging station 145, an archiving station 150, a management server 805, and a workflow server 155. Each of these stations may include one or more process specific laboratory devices (e.g., a microtome at sectioning station 125, microscopes and automated microscopes at imaging station 145, an automated tissue processor and a paraffin embedder at tissue processing and embedding station 120, one or more stainers at the staining stations, an imager, a barcode reader, a printer, etc.). Further, stations 105 to 150, workflow server 155, and management station 805 may each communicate with one another via network 101. By enabling communication among the many laboratory devices associated with the laboratory stations, data regarding a specimen as well as operation of the devices (e.g., hours in use, time per process, operator ID, materials consumed, etc.) may be provided to workflow server 155 for storage in workflow database 160 and other desired processing.

Laboratory environment 100 may include more or fewer stations as those shown in the exemplary diagram of FIG. 1. For example, exemplary arrangements may use only accessioning station 110, tissue processing station 120, advanced staining station 135, and imaging station 145. In addition, the order in which the various stations are shown in FIG. 1A and described throughout the present disclosure, is not intended to be limiting. One of ordinary skill in the art will recognize that such stations may be organized in any desirable order without departing from the scope of the present disclosure.

Network 101 may enable communicative connections between devices within a physical laboratory and may be any suitable network enabling information transfer among electronic devices. For example, network 101 may include an Ethernet LAN, a wide-area network (WAN), and/or the Internet, among other things. Each station or server associated with laboratory environment 100, and each device within a station, may include a communicative connection with network 101, and therefore may be communicatively connected to other laboratory devices present within a physical laboratory. This may allow each laboratory device to request and share data with workflow server 155, among other things.

Receiving station 105 and/or accessioning station 110 may be configured to receive specimens from various sources, including, for example, hospital staff, couriers, and commercial shippers, among others. Receiving station 105 and/or accessioning station 110 may include numerous laboratory devices configured for accomplishing tasks related to receiving and initial preparation of specimens. For example, stations may include a barcode scanner, a printer (e.g., configured for label printing), and/or a workstation configured to receive input from an operator, among others. The term "workstation," as used herein, broadly refers to any computer, personal digital assistant (PDA), mainframe terminal, or other computer-implemented device suitable for interfacing with a user. Further, a workstation consistent with the present disclosure may represent an exemplary workflow server 155 and exemplary management workstation 805, among others. In one example, management workstation 805, workflow server 155, and workflow database 160 may all be part of a single workstation. Therefore, the following description of server 155 may apply to other components of laboratory environment 100 consistent with the present disclosure.

In one implementation, workflow server 155 may include a central processing unit, as well as other components, such as, for example, a display, an input device, and a network controller. Workflow server 155 may display information on a display or at other remote locations, such as, for example, a remote workstation connected via a network.

As noted above, some or all of the devices of receiving station 105 and/or accessioning station 110 may communicate with workflow server 155 via network 101. Stations 105 and/or 110 may then provide specimen data (e.g., patient name, specimen weight, etc.) and operational data (e.g., process time for a specimen, time in use, operator id, etc.) to workflow server 155. Further, one or more of the laboratory devices associated with receiving station 105 and/or accessioning station 110 may include automated features, and/or may involve some manual interaction from an operator.

Because functionality associated with receiving station 105 and/or accessioning station 110 may be similar, stations 105 and 110 may be combined as one station. In such an embodiment, personnel and laboratory devices associated with receiving station 105 and accessioning station 110 may be utilized for performance of the related processes at both stations.

Grossing station 115 may be configured for performing an examination of a specimen, preparing a related description of the specimen according to shape, size, and pathoanatomic findings, and cutting a specimen to fit a specimen cassette or other suitable container. Therefore, grossing station 115 may include one or more laboratory devices, such as, for example, a low power microscope, a barcode scanner, a cassette printer configured to print barcode information to a specimen cassette, and a workstation among other things. The laboratory devices associated with grossing station 115 may also communicate with workflow server 155 via network 101 or other suitable connection, and provide specimen and operational data (e.g., process time for a specimen, time in use, operator id, etc.), among other things, to a user. Further, one or more of the laboratory devices associated with grossing station 115 may include automated features, and/or may involve some manual interaction from an operator.

Tissue processing and embedding station 120 may be configured for processing and embedding a specimen in preparation for sectioning station 125. Tissue processing and embedding station 120 may include one or more laboratory devices, for example, a tissue processor configured to dehydrate a specimen, a paraffin embedding device, a barcode reader, and a workstation, among other things. The laboratory devices associated with tissue processing and embedding station 120 may communicate with workflow server 155 via network 101 or other suitable connection and provide specimen data and operational data (e.g., process time for a specimen, time in use, operator id, etc.), among other things. Further, one or more of the laboratory devices associated with tissue processing and embedding station 120 may include automated features, and/or may involve some manual interaction from an operator.

Sectioning station 125 may be configured to receive an embedded specimen from tissue processing and embedding station 120 and produce slides of a specimen sectioned based on common practice and/or additional instructions. Sectioning station 125 may include one or more laboratory devices, for example, a microtome (i.e., a sectioning device), an oven or other heating device, a barcode reader, a printer (e.g., a slide label printer), and a workstation, among other things. The laboratory devices associated with sectioning station 125 may communicate with workflow server 155 via network 101 or other suitable connection and provide specimen data and operational data (e.g., process time for a specimen, time in use, operator id, etc.), among other things. Further, one or more of the laboratory devices associated with sectioning station 125 may include automated features, and/or may involve some manual interaction from an operator.

H&E staining station 130, advanced staining station 135, and special staining station 140 may be configured for staining specimen slides in accordance with well known practices to those skilled in the art. H&E staining station 130, advanced staining station 135, and special staining station 140 may include one or more stainers (e.g., automated and/or manual devices configured to apply measured amounts of stain to particular specimen slides), a pre-treatment system, stain kits and reagents, a barcode scanner, and a workstation, among others. The laboratory devices associated with H&E staining station 130, advanced staining station 135, and special staining station 140 may communicate with workflow server 155 via network 101 or other suitable connection and provide specimen data (e.g., stains used, etc.) and operational data (e.g., process time for a specimen, time in use, operator id, etc.), among other things. Further, one or more of the laboratory devices associated with H&E staining station 130, advanced staining station 135, and special staining station 140 may include automated features, and/or may involve some manual interaction from an operator. One of ordinary skill in the art will recognize that the staining stations described herein are exemplary, and more or fewer staining stations may be utilized as desired.

Imaging station 145 may be configured for examination of one or more specimen slides for diagnosis. Imaging station 145 may include laboratory devices, such as a microscope, a slide scanner/etcher, a barcode scanner, a printer (e.g., configured to print reports), and a workstation, among other things. The laboratory devices associated with imaging station 145 may communicate with workflow server 155 via network 101 or other suitable connection and provide specimen data (e.g., specimen images) and operational data (e.g., process time for a specimen, time in use, operator id, etc.), among other things. Further, one or more of the laboratory devices associated with imaging station 145 may include automated features, and/or may involve some manual interaction from an operator.

Archiving station 150 may be configured to archive the slides produced from a particular specimen for reference at a later time, and may also archive slide images stored for a period of time via imaging station 145. Archiving station 150 may include laboratory devices, for example, a workstation, a barcode scanner, a printer (e.g., barcode printer), and storage facilities, among other things. The laboratory devices associated with archiving station 150 may communicate with workflow server 155 via network 101 or other suitable connection and provide specimen data (e.g., specimen images) and operational data (e.g., process time for a specimen, time in use, operator id, etc.), among other things. Further, one or more of the laboratory devices associated with archiving station 150 may include automated features, and/or may involve some manual interaction from an operator.

Management workstation 805 may be configured to control laboratory devices associate with any of stations 105 to 150 and/or to provide workflow information or any other information related to specimens and operational data of the laboratory. For example, management workstation 805 may control one or more automated laboratory devices present at the laboratory stations. In such an example, an administrator and/or an operator may wish to simultaneously access information from a microtome station and a tissue processing station without being physically present at one of these two specific laboratory stations. Management workstation 805 may enable such control through network 101. Additional functionality associated with management workstation 805 will be discussed in greater detail below.

Figure 2:
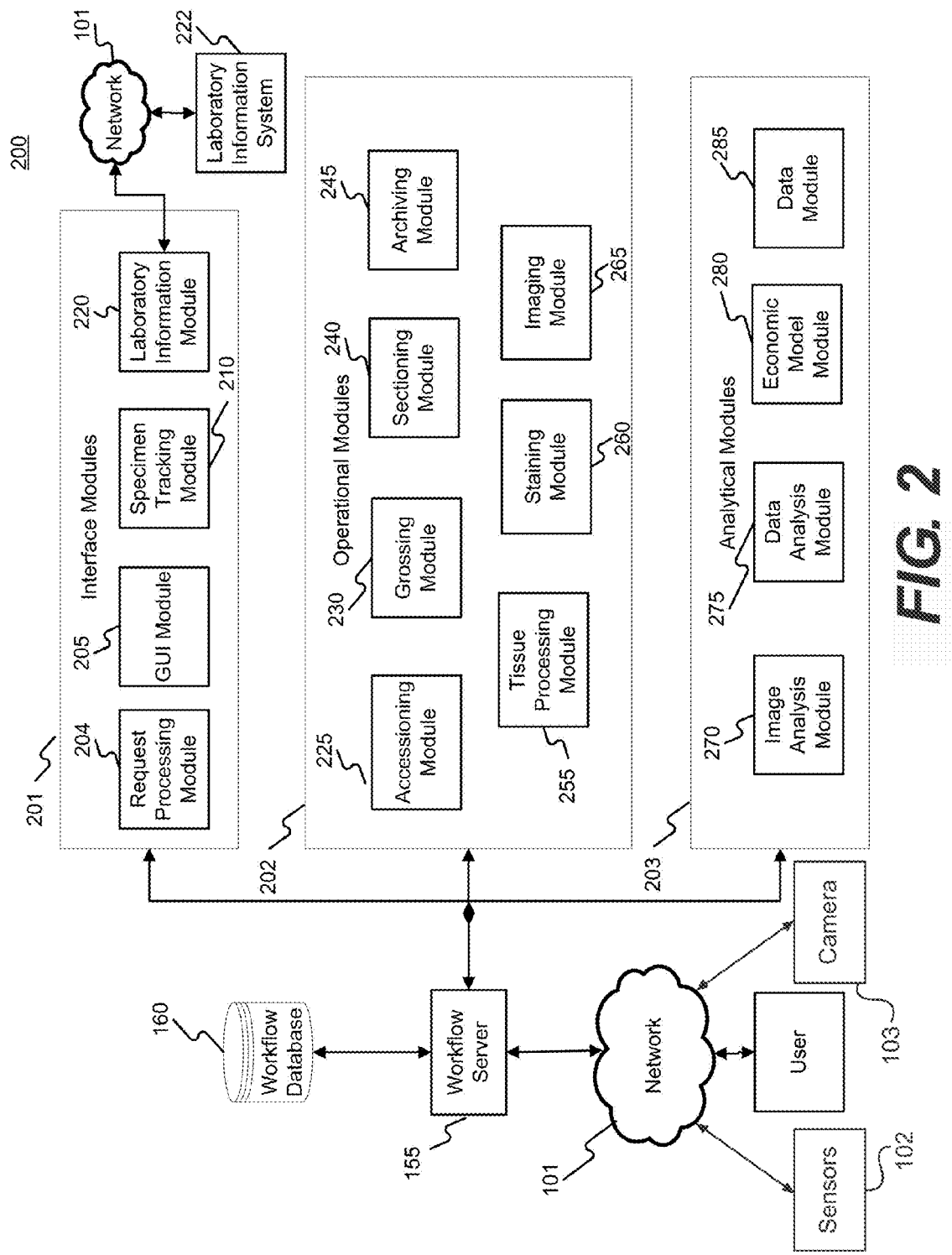
FIG. 2 is an exemplary block diagram representing functional modules that may be associated with a workflow server for purposes of providing functionality associated with a laboratory.

FIG. 2 is an exemplary block diagram representing functional modules that may be associated with workflow server 155. Such modules may enable capture, processing, analysis, and display of workflow data related to a physical laboratory in the context of a virtual laboratory interface. In one arrangement, these functional modules may be stored on a disk in workflow server 155 and/or on a server separate from workflow server 155. Such modules may include compiled computer code providing functions related to visualization and data access (e.g., interface modules 200), lab operations (e.g., operational modules 202), and data analysis (e.g., analytical modules 203). The modules may be written using any programming language, such as, for example C++, Java, Basic, etc. Each module may also present an application programming interface (API) for purposes of data transfer and method access, and may be enabled for remote procedure calls (RPC) and instantiation.

Data associated with interface modules 201, operational modules 202, and analytical modules 203, may be stored, accessed, and processed at detailed levels corresponding to individual specimens, processes, and stations. Such data may also be stored, accessed, and processed at a macro level that includes data from many specimens and stations over any desired period of time.

Operational modules 202 may include an accessioning module 225, a grossing module 230, a sectioning module 240, an archiving module 245, a tissue processing module 255, a staining module 260, and an imaging module 265. Each module will be discussed in greater detail below. While the description below may associate certain functionalities with any particular module, one of ordinary skill in the art will recognize that these modules may include more or less functionality as desired.

Accessioning module 225 may be configured to provide functionality related to shipping and receiving station 105 and/or accessioning station 110. For example, in some embodiments, accessioning module 225 may be configured to receive information related to a received specimen (e.g., patient name, patient ID, received timestamp, etc.) and store such information in workflow database 160 so that the information is associated with or linked to a current specimen. Data provided to accessioning module 225 may be received on an automated basis from laboratory devices associated with receiving station 105 and/or accessioning station 110, and/or from manual entry by a technician of receiving station 105 and/or accessioning station 110 through workflow server via network 101, or other suitable method.

Further, accessioning module 225 may be configured to provide accessioning data previously stored to database 160 in response to a request from workflow server 155 and/or via network 101. Such requests may include, for example, a request for patient data related to a specimen or operational data from a specimen receiving/accessioning procedure. Accessioning module 225 may receive such a request from, for example, analytical modules 203 and/or interface modules 201. Accessioning module 225 may access data from laboratory information system 222 through laboratory information module 220. Such data may be provided through workflow server via network 101, or other suitable method. One of ordinary skill in the art will recognize that more or less functionality than that described herein may be available in each module associated with workflow server 155.

Grossing module 230 may be configured to provide functionality associated with grossing station 115. For example, grossing module 230 may be configured to receive barcode information, specimen description, specimen test plan information, and specimen cassette information, among others, and store such information to workflow database 160 linked to a current specimen. Data provided to grossing module 230 may be received on an automated basis from laboratory devices associated with grossing station 115 (e.g., a cassette printer), and/or from manual entry by personnel associated with grossing station 115 through workflow server via network 101, or other suitable method.

Further, grossing module 230 may be configured to provide information related to grossing station 115 in response to a request from workflow server 155 and/or via network 101.

For example, such information may include providing specimen processing time at grossing station 115, specimen description, a specimen cassette ID, and specimen test plan in response to a request from, for example, analytical modules 203 and/or interface modules 202. In some embodiments, grossing module 230 may be configured to provide additional processing of related information, such as summarizing and/or averaging data entry and cutting times, providing average success rates (e.g., per user), and average cost per error, among others.

Sectioning module 240 may be configured to provide functionality associated with sectioning station 125. For example, sectioning module 240 may be configured to receive barcode information, sectioning time, specimen slide data (e.g., number of slides produced), and sectioning success, among others, and store such information to workflow database 160 linked to a current specimen. Data provided to sectioning module 240 may be received on an automated basis from laboratory devices associated with sectioning station 125 (e.g., a microtome), and/or from manual entry by a technician of sectioning station 125 through workflow server via network 101, or other suitable method.

Further, sectioning module 240 may be configured to provide information related to sectioning station 125 in response to a request from workflow server 155 and/or via network 101. For example, such information may include providing specimen sectioning time, the number of sections from a specimen, and sectioning success status at sectioning station 125, in response to a request from, for example, analytical modules 203 and/or interface modules 202. In some embodiments, sectioning module 240 may be configured to provide additional processing of related information, such as summarizing and/or averaging machine times.

Archiving module 245 may be configured to provide functionality associated with archiving station 150. For example, archiving module 245 may be configured to receive barcode information, patient information, and specimen storage location, and store such information to workflow database 160. Data provided to archiving module 245 may be received on an automated basis from laboratory devices associated with archiving station 150, and/or from manual entry by personnel associated with archiving station 150 through workflow server via network 101, or other suitable method.

Further, archiving module 245 may be configured to provide information related to archiving station 150 in response to a request from workflow server 155 and/or via network 101. For example, such information may include providing specimen location information in response to a request from, for example, analytical modules 203 and/or interface modules 202.

Tissue processing module 255 may be configured to provide functionality associated with processing and embedding station 120. For example, tissue processing module 255 may be configured to receive barcode information, storage cassette information, and dehydration time, among others, and store such information to workflow database 160 linked to a current specimen. Data provided to tissue processing module 255 may be received on an automated basis from laboratory devices associated with tissue processing and embedding station 120 (e.g., an automated dehydrator), and/or from manual entry by technicians associated with tissue processing and embedding station 120 by any suitable method.

Further, tissue processing module 255 may be configured to provide information related to tissue processing and embedding station 120 in response to a request from workflow server 155 and/or via network 101. For example, such information may include providing specimen dehydrating time, paraffin embedding success rate, and operator ID at tissue processing and embedding station 120 in response to a request from, for example, analytical modules 203 and/or interface modules 201. In some embodiments, tissue processing module 255 may be configured to provide additional processing of related information, such as summarizing and/or averaging dehydrating machine times, determining average success rates, and breaking out possible critical points by highlighting errors associated with tissue processing and embedding tasks, among others.

Staining module 260 may be configured to provide functionality associated with H&E staining station 130, advanced staining station 135, and special staining station 140, as well as any other staining stations that may be utilized by the physical laboratory. For example, staining module 260 may be configured to receive barcode information, specimen test plan, stains and reagents used, the number of slides stained, and staining time, among others, and store such information to workflow database 160. Data provided to staining module 260 may be received on an automated basis from laboratory devices associated with H&E staining station 130, advanced staining station 135, and/or special staining station 140 (e.g., an automated stainer), and/or from manual entry by personnel associated with H&E staining station 130, advanced staining station 135, and/or special staining station 140.

Further, staining module 260 may be configured to provide information related to H&E staining station 130, advanced staining station 135, and/or special staining station 140—or other stainers present—in response to a request from workflow server 155 and/or via network 101. For example, such information may include providing stains to be used, staining time, number of slides stained, and staining success status, among others, at H&E staining station 130, advanced staining station 135, and/or special staining station 140. Such a request may also be made by, for example, analytical modules 203 and/or interface modules 201. In some embodiments, staining module 260 may be configured to provide additional processing of related information, such as summarizing and/or averaging staining times from individual stainers present, an average of staining costs per slide, labor hours associated with a staining task, average staining success rates, and other similar data.

Imaging module 265 may be configured to provide functionality associated with imaging station 145. For example, imaging module 265 may be configured to receive barcode information, specimen slide data (e.g., number of slides per specimen), specimen image data, and imaging success status, and store such information to workflow database 160. Data provided to imaging module 265 may be received on an automated basis from laboratory devices associated with imaging station 145, and/or from manual entry by personnel associated with imaging station 145 through workflow server via network 101, or other suitable method.

Further, imaging module 265 may be configured to provide information related to imaging station 145 in response to a request from workflow server 155 and/or via network 101. For example, such information may include providing specimen processing times at imaging station 145, specimen image data, imaging success status, and imaging test plan data, in response to a request from, for example, analytical modules 203 and/or interface modules 201. In some embodiments, imaging module 265 may be configured to provide additional processing of related information, such as summarizing and/or averaging imaging times per slide, imaging success rates, and identifying operator and imager errors, among other things.

Analytical modules 203 may include image analysis module 270, data analysis module 275, economic module 280, and data module 285. Data module 285 may be configured to function as an interface between workflow database 160 and workflow server 155, among other things. For example, data module 285 may implement properties and methods enabling storage and retrieval of data from workflow database 160 via various connection methods (e.g., ODBC). Therefore, data module 285 may provide query processing and dataset return methods configured to standardize data access across modules of workflow server 155. In such an example, one of operational modules 202 may provide a series of data to data module 285, and data module 285 may be responsible for executing a query causing the data to be stored in workflow database 160. Alternatively, when a request for data is made by, for example, one of operational modules 202, data module 285 may parse the request and execute a query related to the request and return the requested data.

Data analysis module 275 may be configured to parse a request related to data associated with the laboratory and/or workflow database 160, analyze data according to the request. For example, data analysis module 275 may receive a request from workflow server 155 to retrieve data related to success rates at tissue processing and embedding station 120. Data analysis module 275 may instantiate tissue processing module 255 and retrieve data based on the request from workflow server 155. Data analysis module may then analyze the data (e.g., to summarize and/or validate the data) and provide the data to economic model module 280 for processing and report generation. Similarly, where a request to store data is initiated by a module associated with workflow server 155, data analysis module 275 may receive and analyze the data for a determination of validity, among other things.

Data analysis module 275 also may be configured to analyze, store, and provide quality control data associated with a physical laboratory. For example, based on a request, data analysis module may obtain random samples of data from workflow database 160 and analyze such data for determinations of, for example, laboratory device performance characteristics, operator performance characteristics, and/or success/error rates. Such analyses may enable a laboratory administrator to address one or more quality control issues associated with one or more laboratory stations. One of skill in the art will recognize that more or less functionality may be provided by data analysis module 275.

Economic model module 280 may be configured to provide data related to economic analysis of workflow data associated with the physical laboratory, among other things. For example, a request may be initiated at management workstation 805 for data related to staining costs at advanced staining station 135. The request may be transmitted via network 101 to workflow server 155, where economic model module 280 may then request data from staining module 260 based on the request. Economic model module 280 may then process such data into a report and return the data to workflow server 155 and on to management workstation 805. Analysis of workflow data by economic module 280 and generation of related workflow reports will be discussed in greater detail below.

Image analysis module 270 may be configured to receive data related to specimen images, among others, and analyze such data in response to a request. For example, specimen image data may be stored in workflow database 160 or other location such as disk 10. Upon receiving a request to view a particular specimen (e.g., by patient ID, barcode, etc.) image analysis module 270 may retrieve one or more images related to a specimen (e.g., digitally scanned slide images) and analyze the image to provide a machine based diagnosis and/or prognosis. Further, analysis may be performed by image analysis module 270, such as, for example, analyzing an image for defects (e.g., to determine slide scanner calibration), among other things. One of skill in the art will recognize that numerous functions may be performed by image analysis module 270 upon further consideration of the present disclosure.

Interface modules 201 may include request processing module 204, graphical user interface (GUI) module 205, specimen tracking module 210, and laboratory information module 220. Interface modules may be configured to provide functionality relating to visualization of interfaces (e.g., virtual laboratory, workflow data reports, etc.) on a display and providing information related to a physical laboratory (e.g., specimen location, lab workflow, etc.).

Request processing module 204 may be configured to receive and process a user request based on input from GUI module 205, or other suitable source (e.g., a laboratory device). For example, a user at management workstation 805 may initiate a request (e.g., a mouse click and/or other selection) to view a current workflow associated with a lab, a specimen status, or other desired request. Such a request may be initiated through an interface present on, for example, management workstation 805, or other suitable location. Request processing module 204 may receive the request through workflow server 155, and parse the request to determine an operation desired by a user. Request processing module 204 may then initiate actions and instantiate modules on workflow server 155 to respond to the request, among other things.

While user selections are generally described in the context of mouse clicks throughout the present disclosure, one of ordinary skill in the art will recognize that user input may be received in numerous ways, such as, for example, by keyboard entry, touch screen entry, voice commands, etc. Any description with regard to mouse-click based input is thus intended as exemplary only and is not intended to be limiting.

GUI module 205 may provide processing for display of data, display of a virtual laboratory component representing the physical laboratory, displaying a workflow associated with the physical laboratory, and receive selections from users at workstations via active components within the GUI (e.g., a clickable area and/or a pushbutton within the virtual laboratory). For example, GUI module 205 may generate a GUI displaying a virtual laboratory component representing a physical laboratory having one or more virtual laboratory stations. These virtual laboratory stations may be virtual representations of any of the stations described with regard to FIG. 1A. In such an example, GUI module 205 may further provide one or more active components such as active areas within the virtual laboratory enabling user input (e.g., a mouse click). Upon receipt of user input (e.g., a selection) GUI module 205 may respond by generating an appropriate interface modification (e.g., a supplemental view of a virtual laboratory station and/or other views). Selections associated with GUI module 205 may also be made by an administrator at management station 805 to control one or more laboratory devices, to display a report containing data requested by the administrator, to track a specimen in the physical laboratory, and/or to view workflow/proposed workflow associated with the physical laboratory.

GUI module 205 may utilize numerous formats and programming languages for providing an interface. For example, in some embodiments, a graphics/animation tool (e.g., Adobe Flash), HTML, and/or XML may be utilized for implementing a particular GUI (e.g., virtual laboratory) through GUI Module 205. In such an embodiment, graphical elements may be designed and stored in a format compatible with the graphics tool (e.g., Adobe Flash format), while text associated with such images may be stored as XML and/or HTML for ease of editing after compilation. One of skill in the art will recognize that other such combinations may be used without departing from the scope of the present invention.

Specimen tracking module 210 may be configured to retrieve and provide information related to the status of one or more specimens in a laboratory. For example, a user may initiate a request based on a patient ID or barcode information (e.g., a scanned barcode) to determine the current status of a specimen in a physical laboratory. Specimen tracking module 210 may retrieve data related to the specimen and provide such data to GUI module 205 for representation within a virtual laboratory component. In such an example, specimen tracking module 210 may also be configured to provide a workflow indication associated with the virtual laboratory. For example, based on a current and/or a proposed workflow, specimen tracking module 210 may provide an indicator and/or path of a hypothetical specimen through a physical laboratory by displaying an appropriate indicator within a virtual laboratory. Workflow visualization will be discussed in greater detail below.

Laboratory information module 220 may be configured to access information from laboratory information system 222 and manipulate such data to enable transfer between laboratory information system 222 and workflow server 155 and/or workflow database 160. Laboratory information systems are known in the art and may be commercially available from vendors including, for example, Cerner Corporation. Each individual laboratory information system 222 may include a data model differing from that associated with other laboratory information systems and workflow database 160. Therefore, to enable data transfer between laboratory information system 222 and workflow database 160 (e.g., automatic data entry at receiving station 105) laboratory information module 220 may act as an interface between workflow server 155, and any of modules 201, 202, and 203 such that data associated with laboratory information system 222 may be obtained, regardless of the laboratory information system vendor. For example, laboratory information system 222 may be configured to store and provide patient and demographic data related to specimens arriving at a laboratory. In such an example, upon receipt and identification of a specimen, laboratory information module 220 may connect to laboratory information system 222 via a network, to obtain specimen data (e.g., physician ordered tests, patient data and demographics, etc.).

Figure 3:
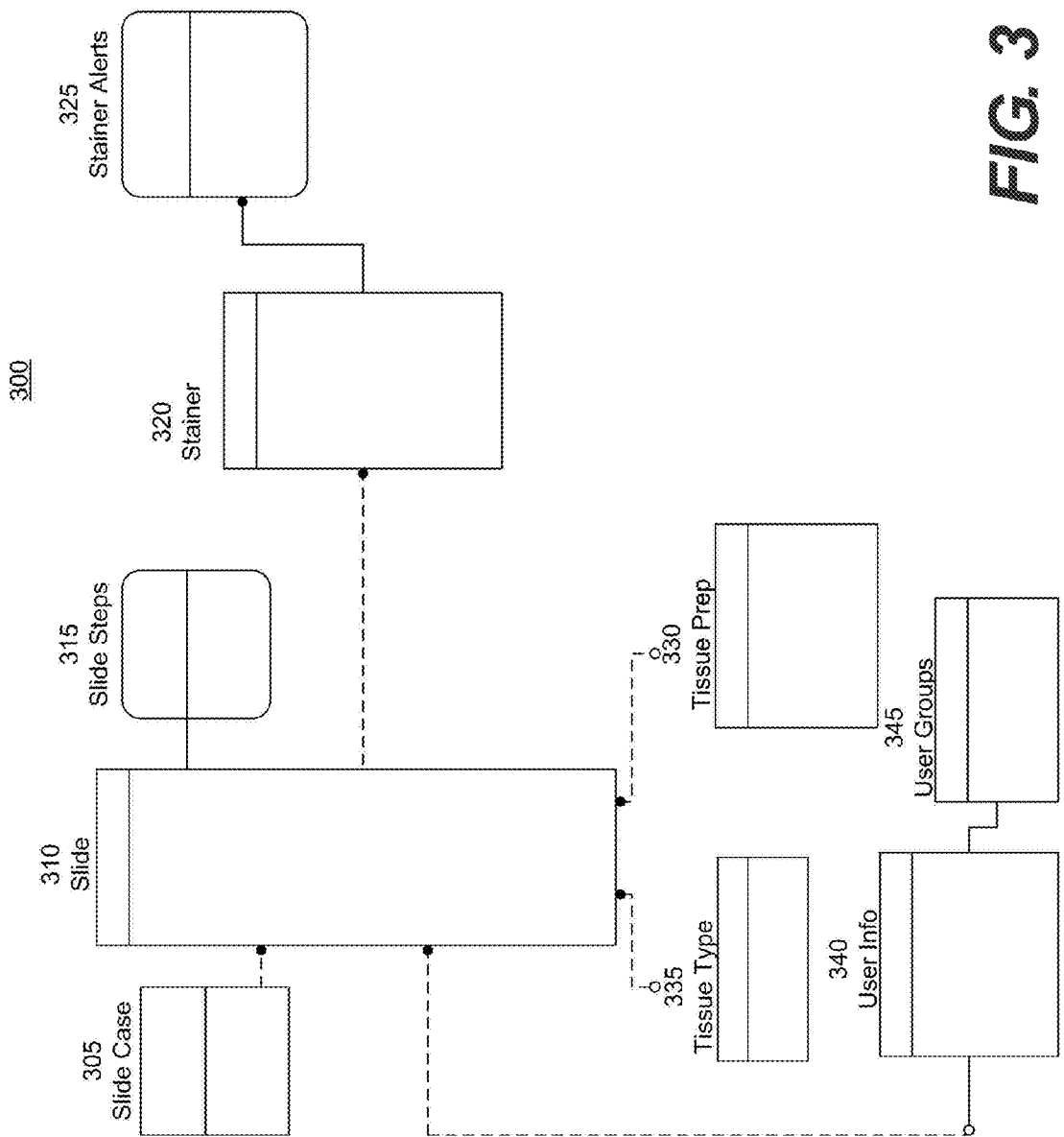
FIG. 3 is a high-level representations of an exemplary physical data model consistent with some embodiments of the present disclosure.

FIG. 3 is a high-level representation of an exemplary physical data model 300 consistent with some embodiments of the present disclosure. As shown in FIG. 3, data model 300 may include a slide case data table 305, a slide table 310, a slide steps table 315, a stainer table 320, a stainer alerts table 325, a tissue prep table 330, a tissue type table 335, a user info table 340, and a user groups table 345. Each of these data tables may store information or data associated with the tracking and displaying of the specimen(s) processed in the laboratory. Such a data model may be implemented within workflow database 160 for purposes of storing, retrieving, and processing workflow data associated with a laboratory, laboratory stations, laboratory devices, and specimens, among other things. The exemplary high-level data model 300 is particularly directed to a lab including a series of automated staining machines. However, one of ordinary skill in the art will recognize that data model 300 is only exemplary and may be modified and/or expanded to suit any laboratory configuration and selection of laboratory devices. Further, more or fewer tables may be provided as desired based on factors such as, types of laboratory devices present in a physical lab, data storage desires, etc.

In the present example, data model 300 depicts data relationships between data tables 305-345. In such a data model, slide table 310 may include relationships to slide case table 305 and slide steps table 315 for purposes of providing lookup information for slide records in slide table 310. Similarly, slide table 310 may include relationships to lookup tables tissue type table 335 and tissue prep table 330 for purposes of identifying tissue characteristics associated with a slide record. Slide table 310 may include relationships to user info table 340 and an indirect relationship to user groups table 345 for purposes of tracking user operations associated with a particular slide record in slide table 310.

In addition, stainer table 320 may represent data associated one particular laboratory device (e.g., a stainer) and may include records related to staining carried out on each slide referenced in stainer table 320. Therefore stainer table 320 may maintain a relationship with slide table 310. For purposes of providing alerts with regard to a particular stainer, and/or slide being stained, stainer table 320 may maintain a relationship with stainer alerts table 325 providing lookup information related to available stainer alerts. It is important to note that data model 300 is exemplary only. One of skill in the art will recognize that data model 300 may modified for use with many different laboratory devices and data structures.

Workflow database 160 may be implemented on a standalone workstation, in conjunction with workflow server 155 (e.g., on the same workstation), or may be split across a server farm based on various factors. Further, workflow database 160 may be implemented using any suitable database management system (DBMS). For example, relational database management software may be used, including, Microsoft SQL Server, Oracle, and/or MySQL, among others. In addition, XML data files, spreadsheet software (e.g., Microsoft Excel) also may be utilized for managing data.

Figure 4:
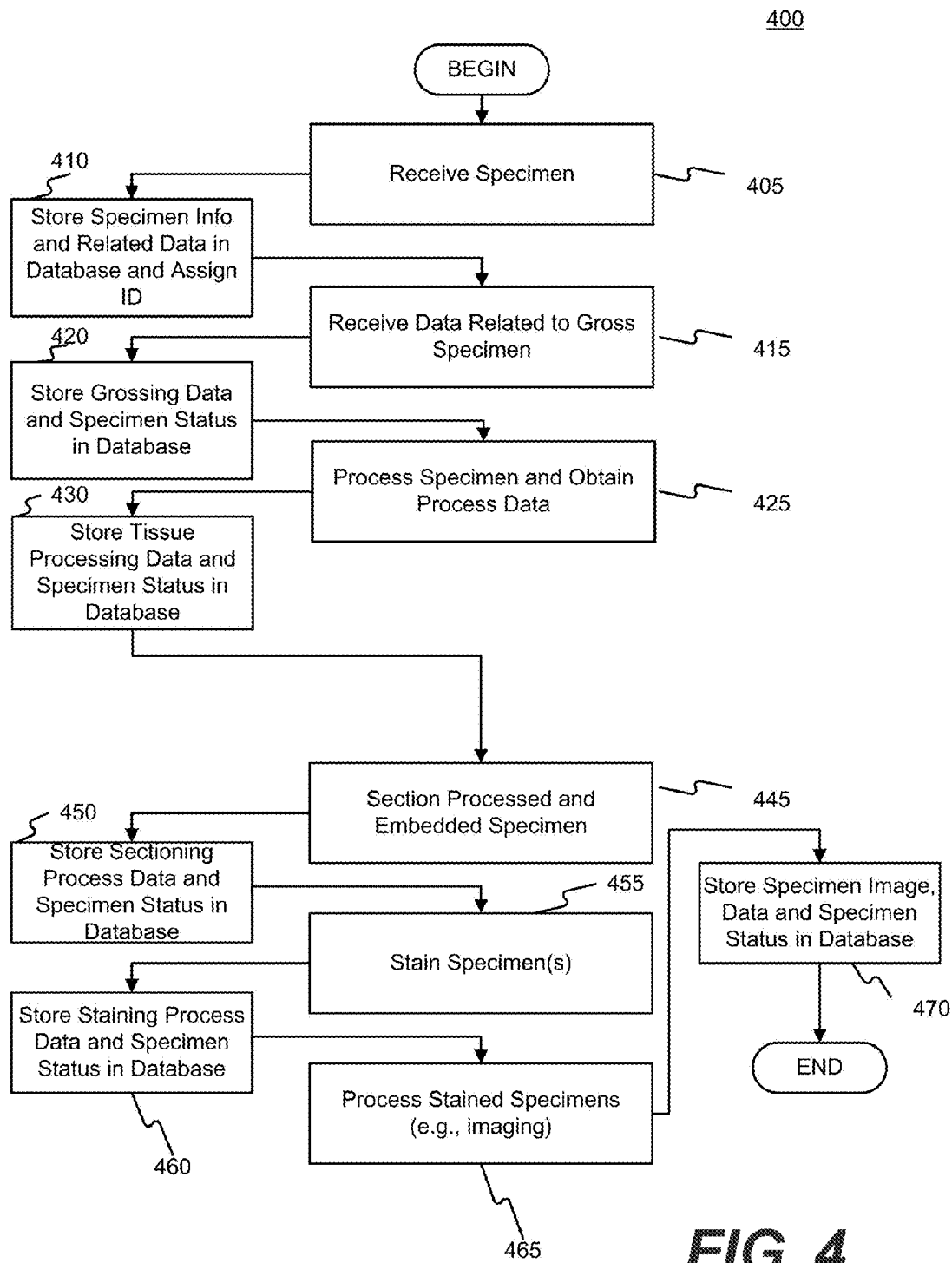
FIG. 4 is a block diagram of an exemplary laboratory workflow and method for collecting data related to one or more laboratory devices associated with a physical laboratory.

FIG. 4 is a block diagram of an exemplary laboratory workflow and method for collecting data related to one or more laboratory devices associated with a physical laboratory. Biological specimens may be received at receiving station 105 and/or accessioning station 110 (step 405). Specimens may be received in jars or as cell smears, and/or in any other suitable form. Further, specimens may also include a request form that lists patient information and history along with a description of the site of origin and a desired test regimen. Additional data related to each specimen may be entered into a workstation associated with receiving station 105 and/or accessioning station 110. Once information has been entered into the workstation, specimens may be accessioned by giving them a unique identifier that may be used to uniquely identify each specimen for each patient throughout the workflow of the lab (step 410). A unique ID may enable tracking and tracing of each specimen as related data is stored in workflow database 160. Following accessioning, barcode case information labels may be printed for the request form and/or the specimen container. This may enhance traceability and assist in elimination of errors originating from, for example, redundant data entry throughout the laboratory process. In some embodiments, derived specimens may be derived by cutting a portion of an original specimen. For example, a tissue block with a unique identifier may be sectioned using a microtome at a sectioning station 240 and each derived specimen may be placed on a separate microscope slide labeled with a separate unique identifier. The unique identifiers of the derived specimens may then be associated with the unique identifier of the tissue block so that throughout the workflow, a true positive ID is maintained and tracked for each specimen and derived specimen. In some embodiments of the present invention, specimens may be tracked at any stage in the process from management station 805, or other suitable device, through connectivity to network 101, workflow server 155, and specimen tracking module 210.

During accessioning of a specimen, workflow data related to one or more processes undertaken at receiving station 105 and/or accessioning station 110 also may be captured and stored to workflow database 160. For example, data such as a user ID associated with an operator, specimen IDs, specimen status, total time in accessioning, label printer operation time, workstation operation time, etc. may be captured (step 410). Such data may be processed by accessioning module 225 and stored at workflow database 160. One of ordinary skill in the art will recognize that more or less data may be captured based on factors such as administrative desires and cost, among others.

After being accessioned, specimens may be taken to grossing station 115 to undergo grossing processes and data capture (step 415). Larger sectional cuttings of the specimen may be made at grossing station 115 with additional related descriptions noted and transmitted to workflow server 155 via a computer or other suitable device at grossing station 115 (step 420). Selected specimens may then be placed in cassettes (e.g., plastic specimen cassettes), and/or other suitable containers, along with the unique identifier and barcode affixed (e.g., using a cassette printer). Providing the unique identifier on a specimen cassette or other container may further assist in reducing error rates and may save time for the operator operating grossing station 115, and subsequent stations.

During grossing of a specimen, workflow data related to one or more processes undertaken at grossing station 115 also may be captured and stored to workflow database 160. For example, data such as a user ID associated with an operator, specimen IDs, specimen status, total time in grossing, cassette printer operation time, workstation operation time, success information, etc. may be captured (step 420). Such data may be processed by grossing module 230 and stored at workflow database 160. One of ordinary skill in the art will recognize that more or less data may be captured based on factors such as administrative desires and cost, among others.

Following grossing of a specimen, the specimen maybe processed and embedded at tissue processing and embedding station 120 (step 425). At tissue processing and embedding station 120, a specimen may undergo a preservation process called fixation, among other things. Fixation may be performed to slow and/or stop natural tissue degradation and may be performed automatically in a automatic tissue processor (not shown). Automatic tissue processor may dehydrate the tissue and followed by a cleaning step with an organic agent (e.g., xylene).

During the process of embedding, a dehydrated specimen may be embedded in a substance such as, for example, paraffin wax. This paraffinization may be performed using a mould to make blocks including the specimen to facilitate the sectioning process (step 445). Proper tissue orientation may be desirable when making a paraffin block such that sectioning may be performed correctly.

Prior to departure from tissue processing and embedding station 120, specimens may be sorted according to unique ID number and a priority. Such sorting may be facilitated by one or more laboratory devices associated with tissue processing and embedding station 120. For example, a barcode reader may be used to scan cassettes for tracking and administration of specimens, and the data logged to workflow database 160.

During processing and embedding of a specimen, workflow data related to one or more processes undertaken at tissue processing and embedding station 120 may be captured and stored to workflow database 160 (step 430). For example, data such as a user ID associated with an operator, specimen IDs, specimen status, dehydration time in the automatic tissue processor, wash time in the automatic tissue processor, quantity of organic solvent used, paraffin block orientation, and processing success information, among other things, may be captured. Particularly, automated devices such as an automated processor and dehydrator may provide additional information and data related to processing undertaken at tissue processing and embedding station 120. Such data may be processed by tissue processing module 255 and stored at workflow database 160. One of ordinary skill in the art will recognize that more or less data may be captured based on factors such as administrative desires and cost, among others.

Once processed and embedded, a specimen may sectioned at sectioning station 125 (step 445). At sectioning station 145 embedded tissue blocks may be cut into thin sections using a cutting device, for example, a microtome. Tissue sections may have a thickness of 3-4 microns, and a number of slides per specimen may be generated from the sections made by the cutting device. The sections may be collected on slides (e.g., glass slides), and labeled utilizing one or more bar-code slide labeling machines. Such machines may be automated and may utilize information read from a specimen cassette barcode or other container for purposes of producing one or more slide labels. The number of slides being determined by such things as, staining requirements (e.g., routine staining (H&E), immunohistochemistry (IHC), and/or special stains), success rates, etc.

Once the sections are placed on labeled slides, the slides may be placed in a slide rack and dried in a heating device, such as, for example, an oven for baking to ensure that a specimen adheres to a microscope slide throughout processing. Pretreatment such as deparaffinization (i.e. heating and/or dissolving paraffin to remove it from the sample) may also take place. Other pretreatment may include antigen retrieval to uncover epitopes for IHC staining or to denature DNA for molecular staining. As slides are moved from station to station, heating device racks may be the same racks or substantially similar racks to those used in one or more steps at staining stations 130-140. This may aid in shortening tissue handling times and minimizing errors.

Cassettes with remaining specimen material may then be cataloged and saved in boxes. Barcodes affixed to slides departing from sectioning station 125 may be scanned and information logged to workflow database 160, and/or other suitable location, along with other workflow data related to processes performed at sectioning station 125 (step 450). For example, data such as a user ID associated with an operator, specimen IDs, specimen status, slide count, storage rack ID, time in heating device, heating device temperature, storage box location (e.g., for remaining specimen), and slide preparation success information, among other things, may be captured. Particularly, automated devices such as an automated microtome may provide additional information and data related to processing undertaken at sectioning station 125. Such data may be processed by sectioning module 240 and stored at workflow database 160. One of ordinary skill in the art will recognize that more or less data may be captured based on factors such as administrative desires and cost, among others.

Once a specimen has been sectioned, the labeled slides may be stained at one or more of H&E staining station 130, advanced staining station 135, and/or special staining station 140 (step 455). In some embodiments, staining may be performed on an automated stainer with minimal operator interaction. In other embodiments, particularly where advanced staining (e.g., IHC) and special stains are desired, manual staining, and/or automated staining systems may be used (e.g., Artisan Staining System by Dako). Once stained, slides may be cover-slipped with a solution depending on a mounting media. Slides belonging to particular patient cases may be collected and checked for proper staining.

Barcodes associated with slides stained at H&E staining station 130, advanced staining station 135, and/or special staining station 140 may be scanned and related information logged to workflow server 155, and/or other suitable location, along with other workflow data related to processes performed at H&E staining station 130, advanced staining station 135, and/or special staining station 140 (step 460). For example, data such as a user ID associated with an operator, specimen IDs, specimen status, slide count, slide IDs, stains utilized, amount of each stain used, time at staining station, slide rack ID, and slide staining success information, among other things, may be captured. Particularly, automated devices such as an autostainer may provide additional information and data related to the staining processes undertaken at H&E staining station 130, advanced staining station 135, and/or special staining station 140. Such data may then be processed by staining module 260 and stored at workflow database 160. One of ordinary skill in the art will recognize that more or less data may be captured based on factors such as administrative desires and cost, among others.

Following staining, specimen slides may be processed at imaging station 145 (step 465). Processes at imaging station 145 may include visual examination of the stained slides through a microscope and/or other similar device to perform diagnosis and/or prognosis. Barcodes associated with the stained slides may be scanned and data stored to workflow database 160 by staining module 260. This may enable an identified specimen to be recalled to, for example, allow configuration of an imager and/or to remotely display imaging data. In some embodiments, a specimen slide imager may be an automated imager (e.g., ACIS III by Dako). Specimen slides may be loaded into the automated imager using the current slide rack, or alternatively, a special slide rack configured for the imager. An imager may be calibrated and configured to send various data to workflow server 155. As specimens are scanned, an image may be displayed on a workstation display. Further, a report template may allow reports to be generated from the image data, and may support a range of administrative requirements. An operator may then fill in the remaining information on the report (e.g., through a keyboard at the workstation).

Barcodes associated with slides examined and imaged at imaging station 145 may be scanned and related information logged to workflow database 160, along with other workflow data related to processes performed at imaging station 145 (step 470). For example, data such as a user ID associated with an operator, specimen IDs, specimen status, slide IDs, image data, diagnosis/prognosis, time to image, and imaging success information, among other things, may be captured. Particularly, automated devices such as an automated imager may provide additional information and data related to the staining processes undertaken at imaging station 145. Such data may then be processed by imaging module 265 and stored at workflow database 160. One of ordinary skill in the art will recognize that more or less data may be captured based on factors such as administrative desires and cost, among others.

Referring to FIG. 1, at each of stations 105-150 supply data may be captured. Supply data may include, for example, information related to supplies used in lab operations. For example, supply data may include the number of available slides, coverslips, specimen containers, cassettes, and other containers; quantity of available reagents, solvents, buffers, and other fluids; available quantity of paraffin wax; amount of available labels, paper, slide racks, printer cartridges, and other information related to supplies utilized in laboratory operations. Supply data may be entered manually via a data entry device by a user into a database (e.g., workflow database 160). Alternatively, supply data may be entered automatically into workflow database 160 via signals received from one or more sensors 102 configured to track supplies. For example, a pressure sensor may be used to measure a volume of reagent or other fluid remaining in a laboratory device, such as a stainer. A bar code reader or RFID, for example, may be used to track supplies, such as the number of remaining slides or containers. It is contemplated that sensors may be associated with one or more modules 225-265. One of ordinary skill in the art will recognize upon consideration of the present disclosure that numerous other types sensors or methods may be utilized to track supplies, and those described herein are intended as exemplary.

In some embodiments consistent with the present disclosure, it may be desirable to provide a computer based interface to, for example, administrators, sales staff, trainers, etc., for purposes of visualizing workflow, potential workflow improvements, and laboratory economic data, among other things, associated with a physical laboratory. This interface may be implemented as a "virtual laboratory" displayed on a display associated with a computer workstation (e.g., management workstation 805) and/or other suitable devices. Utilizing systems and methods of the present disclosure, implementations of such an interface may be realized. While describing FIGS. 5-7 below, reference also may be made to FIGS. 8-15H.

Utilizing systems and methods discussed herein, one or more workflows may be modeled. A modeled workflow may be based on data collected utilizing methods such as those described with regard to FIG. 4, or, alternatively, modeling may include creating data for a workflow, for example, for purposes of demonstrating improvements that may be obtained when changes in workflow are made. One of ordinary skill in the art will recognize upon consideration of the present disclosure that numerous other workflows may be possible, and those described herein are intended as exemplary.

Figure 5:
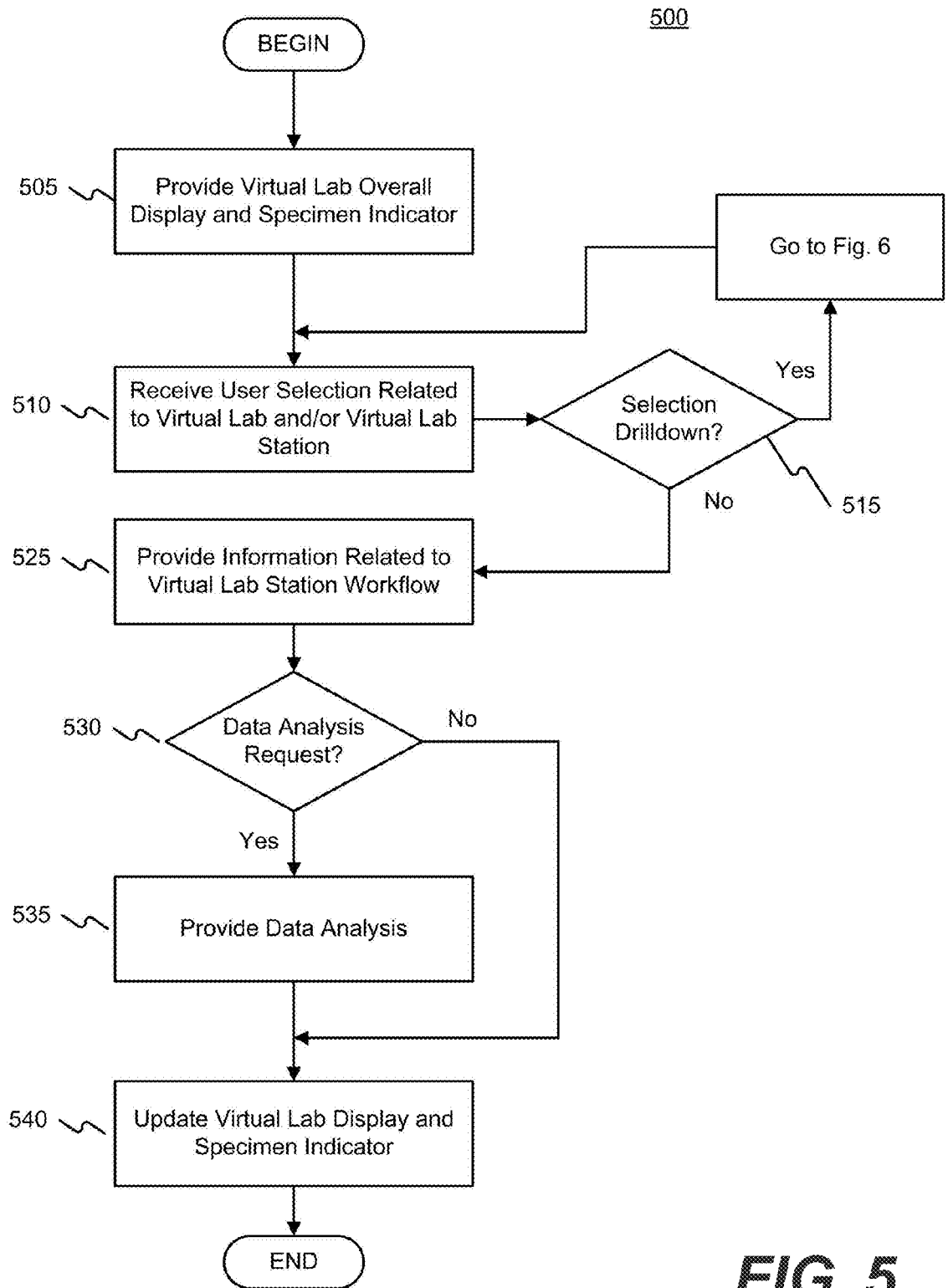
FIG. 5 is a block diagram showing an exemplary method for providing workflow information associated with a physical laboratory.

FIG. 5 is a block diagram showing an exemplary method for providing workflow information associated with a physical laboratory. Upon initiating a computer application consistent with embodiments disclosed herein, a user may be presented with a virtual laboratory component representing a physical laboratory. Such an interface may be provided by, interface modules 201 associated with workflow server 155, among others.

Figure 8:
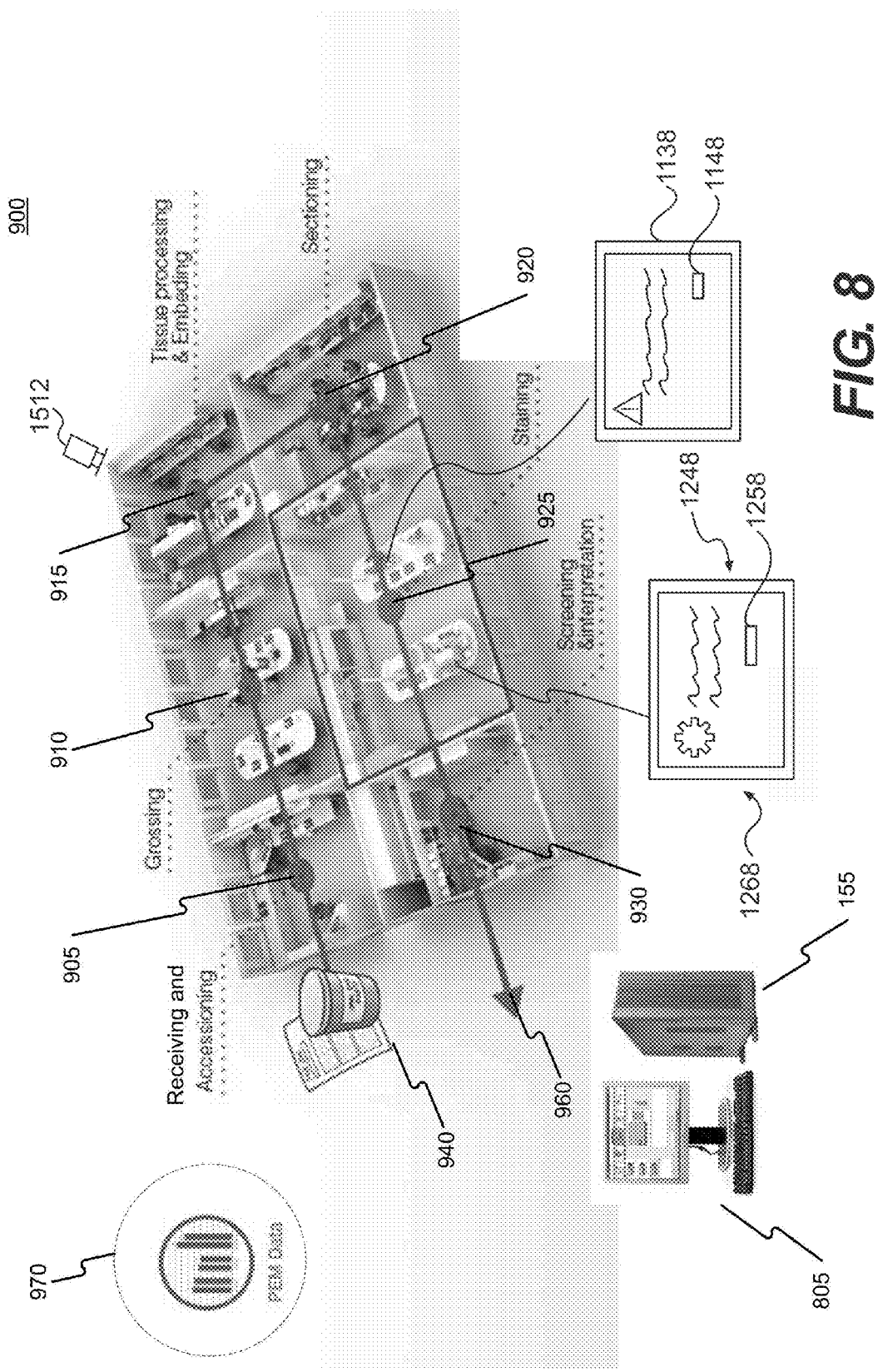
FIG. 8 is an exemplary view of a virtual laboratory consistent with some embodiments of the present disclosure.

An example of a virtual laboratory component 900 is shown FIG. 8. Virtual laboratory 900 may include one or more virtual laboratory stations, including, for example, virtual receiving and accessioning station 905, virtual grossing station 910, virtual tissue processing and embedding station 915, virtual sectioning station 920, virtual staining station 925, and virtual imaging station 930. Virtual laboratory 900 may also include a specimen indicator 940, a workflow indicator 960, and one or more active components associated with virtual laboratory 900 (e.g., economic data access component 970) enabling receipt of a user selection. Virtual laboratory 900 may be associated with a physical laboratory. For example, one or more of the virtual laboratory stations 905-930 (e.g., accessioning station 905, virtual grossing station 910, embedding station 915, etc.) may correspond to and represent a station in a physical laboratory (i.e., 1:1 correspondence).

It is also contemplated that virtual laboratory 900 may be associated with and represent a plurality of physical laboratories. Each virtual laboratory station may be associated with and represent a plurality of physical laboratory stations (i.e., 1:n correspondence). For example, virtual accessioning station 905 may represent and provide data received from a plurality of physical accessioning stations. The data may include, workflow data, economic data, supply data, etc. When virtual laboratory 900 is associated with a plurality of physical laboratories, the data provided by virtual laboratory 900 and each virtual laboratory station may be an aggregation of data received from the physical laboratory stations. The aggregation of data may be represented as an average, a weighted average, a median, or another representation of an aggregation of data known in the art. Alternatively or additionally, virtual laboratory stations 905-930 may provide representative data for each individual physical station. For example, a user may be provided with data from an individual physical accessioning station out of a plurality of physical accessioning stations by selecting the desired station from, for example, a list or pull down menu. It is contemplated that the data provided by virtual laboratory 900 and virtual laboratory stations 905-930 may capture multiple dimensions (e.g., time and location). In one embodiment, data may be provided for one or more locations (e.g., a single physical station, multiple physical stations, a single physical laboratory, or multiple physical laboratories) at given time point or over a period of time.

In addition to being a link to a physical laboratory, virtual laboratory may be utilized as a training, educational, or sales tool. In this form, virtual laboratory 900 may utilize stored or simulated data to produce exemplary workflows.

Elements of virtual laboratory 900 will now be discussed in greater detail. Specimen indicator 940 may be configured to indicate a specimen location, a specimen station, and a specimen flow in relation to the one or more virtual laboratory stations. Such indication may be accomplished by applying various visual techniques to specimen indicator 940. For example, where a data request indicates a desire to determine a current status associated with a specimen, request processing module 204 may utilize specimen tracking module 210 to obtain data about a requested specimen. In response, GUI module 205 and specimen tracking module 210 may cause specimen indicator 940 to be located in a virtual laboratory station consistent with the actual physical location of the specimen for which status was requested. Further, as noted above, a specimen may maintain different states depending on what laboratory stations have processed it. For example, depending upon which laboratory station has processed the specimen, the specimen may be received in jars, placed in a cassette, cut to slides, etc. Specimen indicator 940 may thus indicate the current state of the specimen as being in either a jar, a cassette, or a slide state. Moreover, specimen indicator 940 may thus become animated to demonstrate motion through virtual laboratory 900, and, may change in appearance based on a current state of a specimen with regard to a laboratory station. For example, specimen indicator 940 may depict a jar and request form when the specimen has not yet entered virtual grossing station 910. Upon entering grossing station 910, specimen indicator 940 may depict a barcoded cassette to indicate the specimen's new state. Upon arrival at virtual sectioning station 920, specimen indicator 940 may then depict a glass slide. One of ordinary skill will recognize that such depictions or appearances are exemplary only and other appearances may be applied to specimen indicator 940 to demonstrate a specimen's state, among other things.

Further, in some embodiments consistent with an anatomical pathology laboratory, specimen indicator 940 may be configured to accurately depict changes in the state, quantity, and/or workflow of different types of specimens. For example, at grossing station 115, an organ or a large mass of tissue may be measured, photographed, or described (e.g., by its size, condition, or appearance). Grossing station 115 may also perform different physical processes depending on types of tissue associated with the specimen. Specimen indicator 940 and text component 1020 (described in more detail with respect to FIG. 10A) may thus be configured to depict differences in the specimen's state and/or its position in the workflow.

In further embodiments, sections of tissue to be processed may be identified and derived from an organ or larger mass of tissue. In such cases, some variance in processing times or quality may occur depending on the technician's skill and experience, among other things. Operational modules 202 may be configured to measure statistical data obtained from the respective laboratory stations and analytical modules 203 may be configured to analyze the statistical data to provide high level statistical trend data. For example, management station 805 may display statistical trend data showing a grossing quality and time for each technician working at grossing station 115.

Additionally, at sectioning station 920, sections of a tissue specimen may be cut, floated on a water bath, and then scooped onto a slide. However, sometimes a fold, tear, or air bubble in the tissue section may form as it is put on the slide, requiring that the slide be discarded and a new slide prepared. Operational modules 202 may thus record the time between slides or even the number of slides that had to be replaced. Analytical modules 203 may thus process such high-level quality control information for display at management station 805.

In other embodiments, at any of stations 105-150 and 805, laboratory environment 100 may use color-coding or other visual cues associated with tissue cassettes, slides, labels, and other containers to identify specimens or types of specimens. Since different types of specimens may follow a different workflow, specimen indicator 940 may be configured to accurately reflect the particular appearance and workflow of each specimen type. By doing so, systems consistent with the present disclosure may visualize the workflow for purposes of technician training or quality control.

Virtual laboratory stations 905-930 may be configured to represent laboratory stations associated with a physical laboratory and may enable access to data, laboratory devices, and descriptions of processes associated with the physical laboratory stations, among other things. Virtual laboratory stations 905-930 may also include one or more active components enabling a user selection (e.g., a clickable area) associated with virtual laboratory 900. For example, virtual receiving and accessioning station 905 displayed within virtual lab 900 may provide a virtual representation of receiving station 105 and accessioning station 110. Access to data obtained during steps 405 and 410 of FIG. 4 may be enabled through virtual receiving and accessioning station 905, as well as descriptions of processes undertaken at an exemplary physical receiving station 105 and accessioning station 110. Alternatively, physical receiving station 105 and accessioning station 110 may be represented as individual virtual stations as desired. An active component associated with virtual receiving and accessioning station 905 may, therefore, be enabled to receive a user selection (e.g., user mouse-click) related to virtual receiving and accessioning station 905 and/or other virtual laboratory stations (step 510). In some embodiments, an active component may enable a user to select within an active component associated with virtual lab 900 to first access information related to a virtual laboratory station and then to select again for "drilling down" to a supplemental view of a selected virtual laboratory station.

Upon initial selection of a virtual laboratory station, specimen indicator 940 may follow workflow indicator 960 to the virtual laboratory station selected by the user and active components associated with the selected virtual laboratory may become enabled. Alternatively, such active areas may be enabled continuously.

Figure 9A:
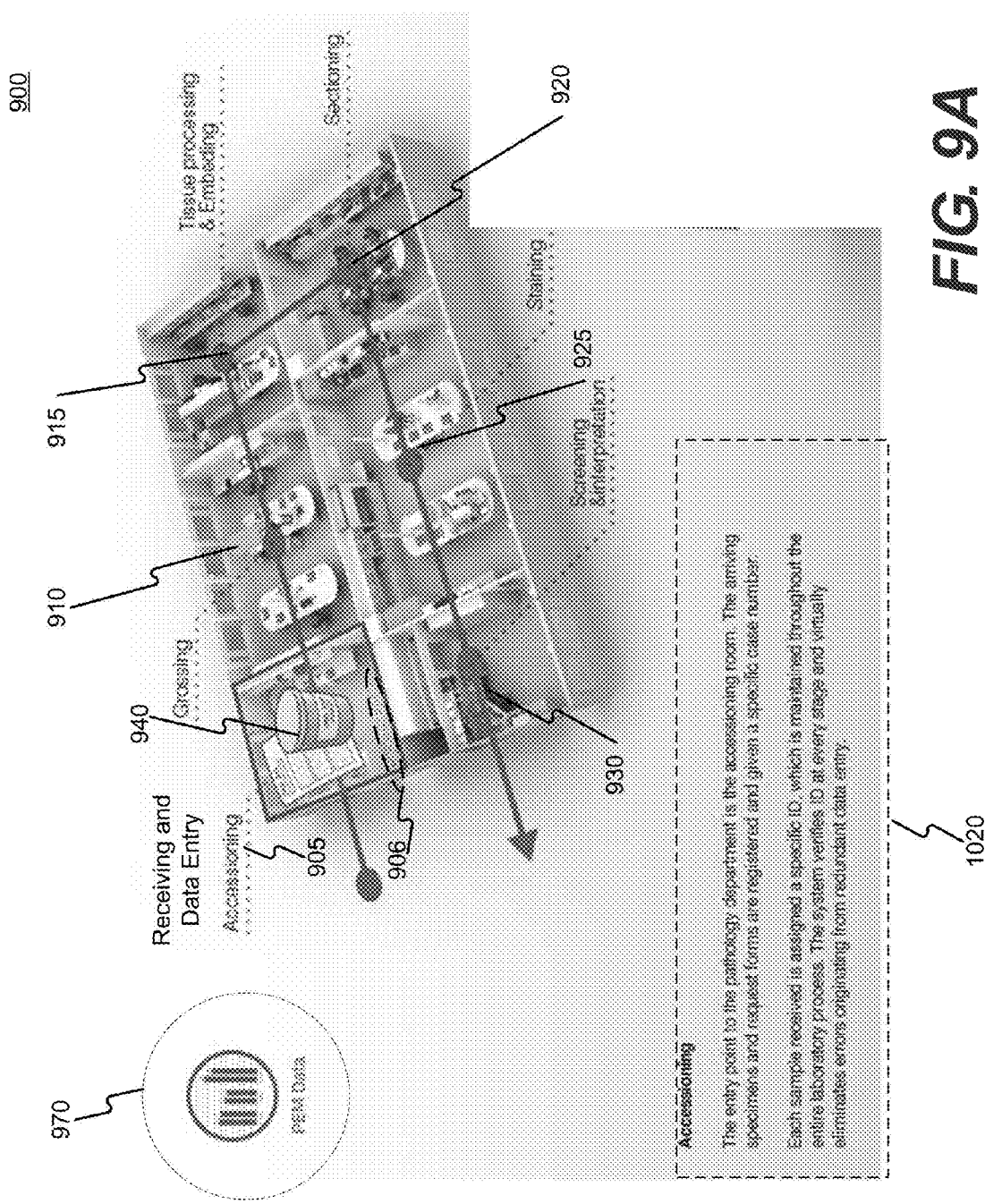
FIG. 9A is an exemplary depiction of a virtual laboratory following a user selection of a virtual receiving and accessioning station.

FIG. 9A is an exemplary depiction of virtual laboratory 900 following a user selection of virtual receiving and accessioning station 905, while FIGS. 10A, 11A, 12A, 13A, and 14A are exemplary depictions of virtual lab 900 following initial selection of other virtual laboratory stations. Virtual laboratory 900 may display a text component 1020 and exemplary active components associated with virtual laboratory 900 (e.g., receiving and accessioning station 905) upon initial selection of a virtual laboratory station. Text component 1020 may be configured to provide text-based information related to workflow, processes, and laboratory devices, among other things. Text component 1020 may display such information based on user selections and/or based on a current workflow associated with virtual lab 900. For example, where a user selection (e.g., user mouse click) indicates virtual receiving and accessioning station 905, text component 1020 may provide a high-level description of tasks carried out at virtual receiving and accessioning station 905, among others. As shown, specimen indicatory has followed workflow indicator 960 to virtual receiving and accessioning station 905 and may depict a current state of a specimen (e.g., received in jars with a request list).

Figure 6:
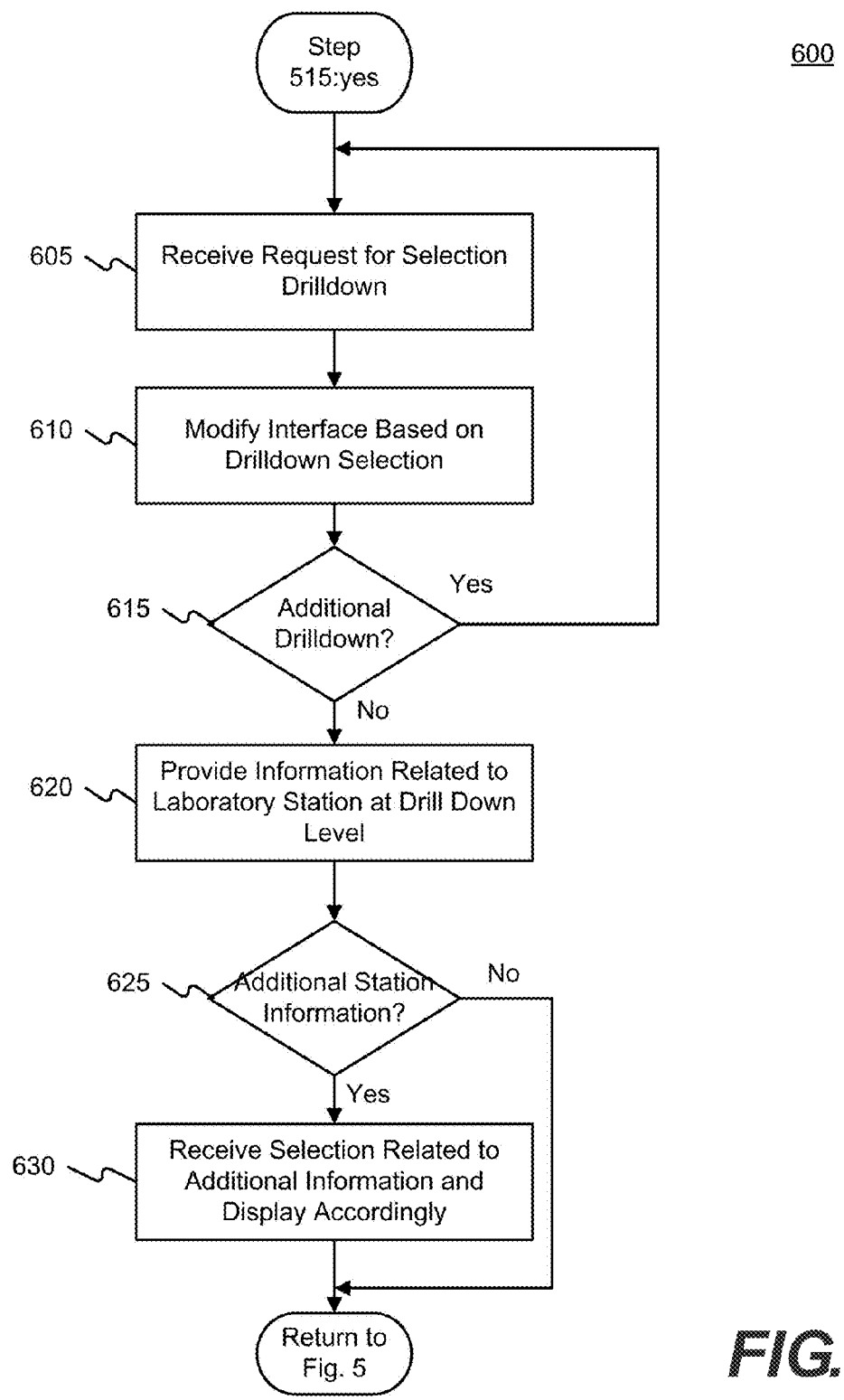
FIG. 6 is a detailed block view of a method for providing drilldown views of virtual laboratory stations.

Active component 906 may allow a user to click for purposes of "drilling down" to supplemental component view (e.g., a more detailed view) associated with virtual receiving and accessioning station 905. Upon receiving such a drill down request (step 515:yes), a supplemental component view of a selected virtual lab element may be displayed (flow passes to FIG. 6). FIG. 6 is a detailed block view of a method for providing drilldown views of virtual laboratory stations. For example, where a user has selected an active component associated with a virtual laboratory station of virtual laboratory 900 (e.g., virtual receiving and accessioning station 905) (step 605), the interface may be modified based on the user's selection (step 610). For example, upon selecting a supplemental component associated with virtual receiving and accessioning station 905, the interface may be modified by interface modules 201, operational modules 202, and analytical modules 203, among others, to provide a supplemental component view of virtual receiving and accessioning station 905 (step 610).

Figure 9B:
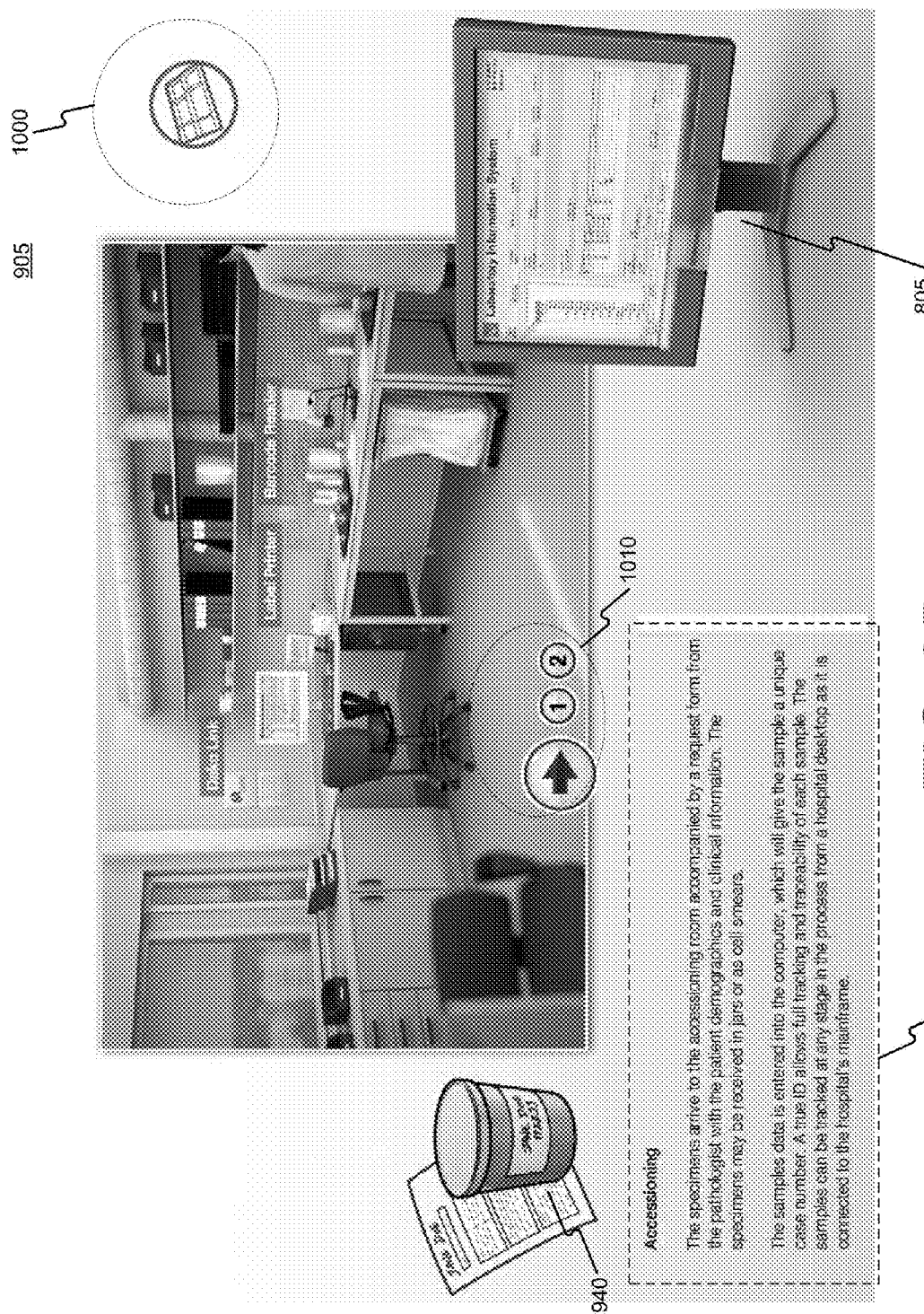
FIG. 9B is an exemplary representation of an interface providing a supplemental component associated with a virtual receiving and accessioning station.
Figure 10B:
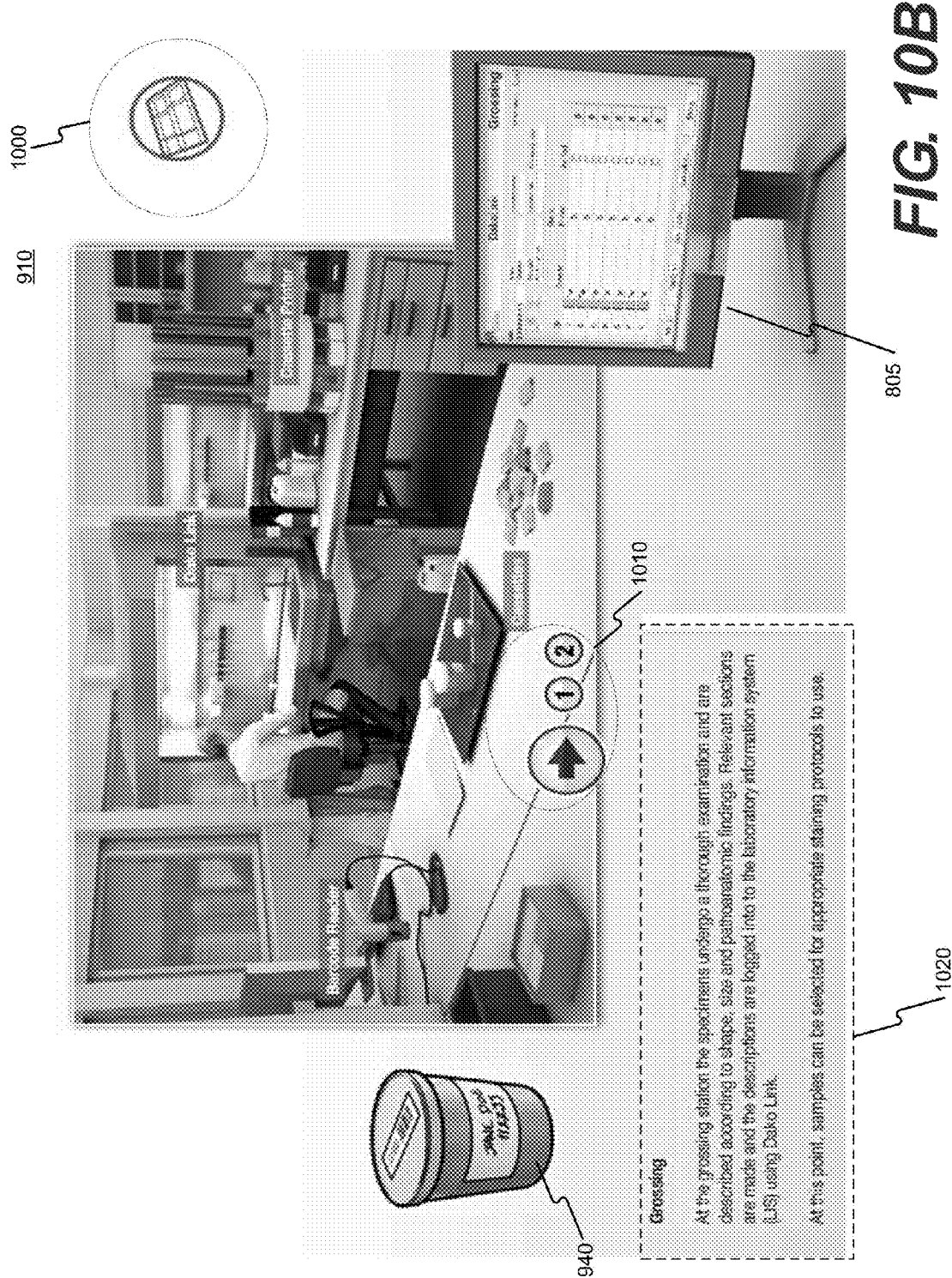
FIG. 10B is an exemplary representation of an interface providing a supplemental component associated with a virtual grossing station.
Figure 11A:
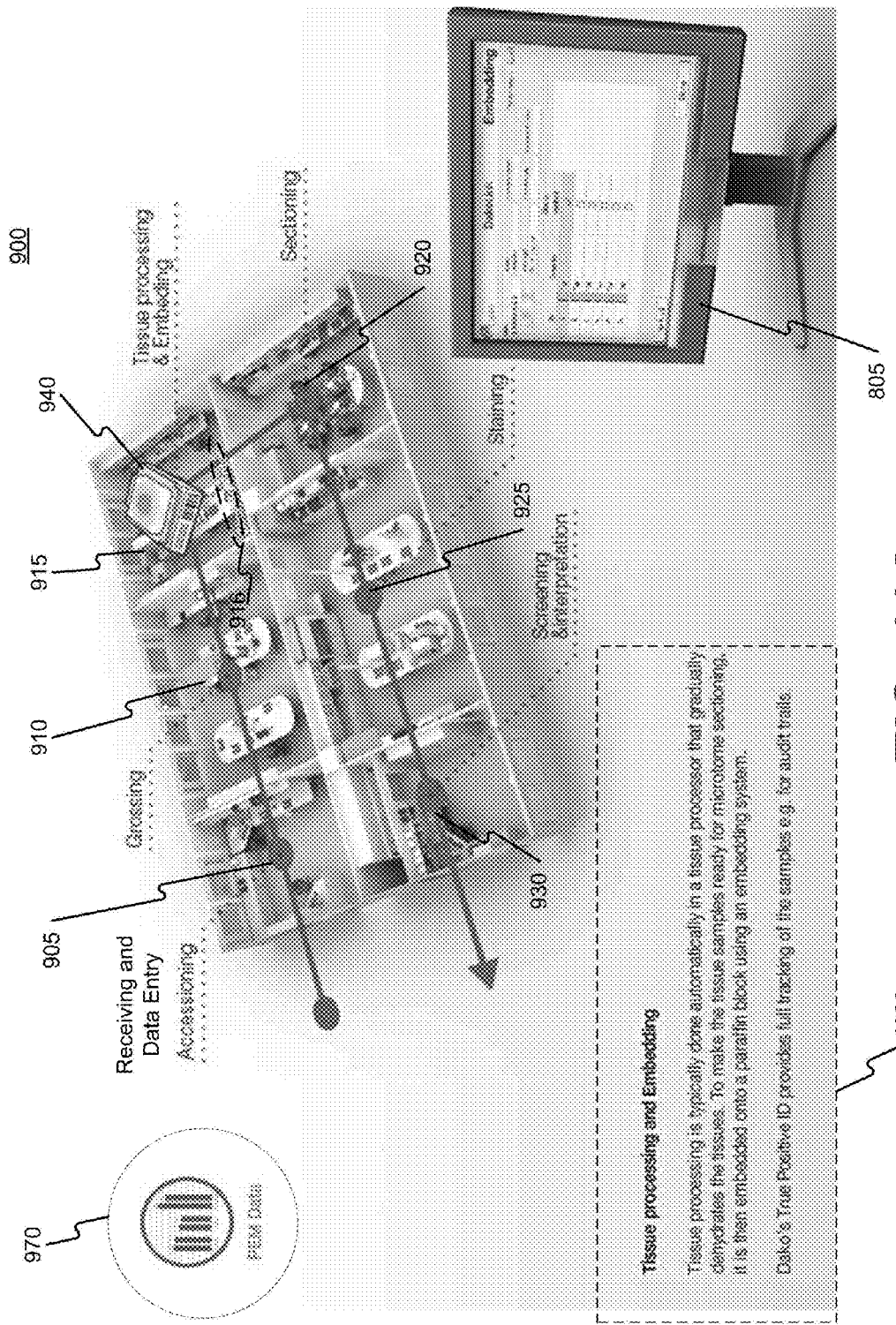
FIG. 11A is an exemplary depiction of a virtual laboratory following a user selection of a virtual tissue processing and embedding station.
Figure 11B:
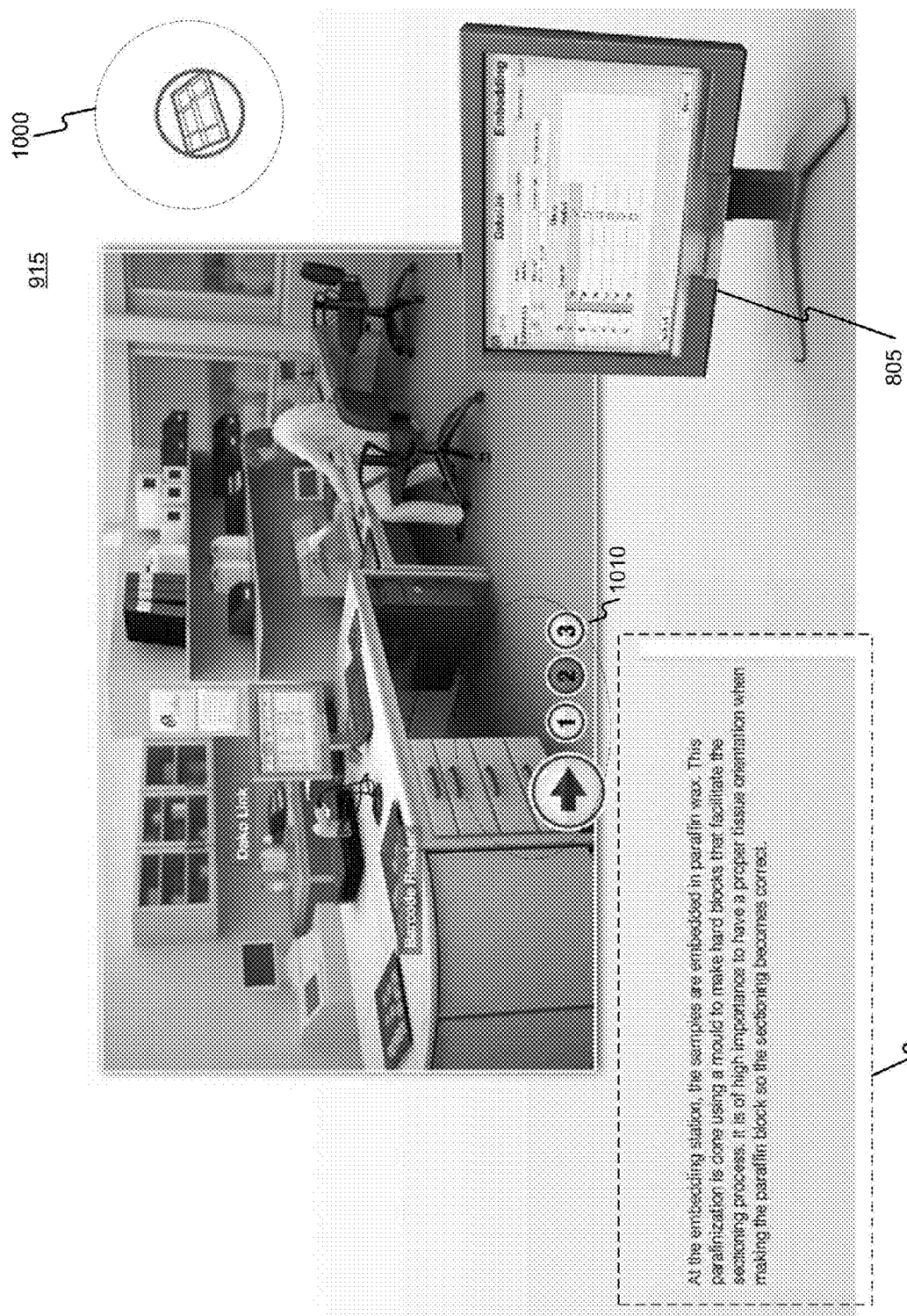
FIG. 11B is an exemplary representation of an interface providing a supplemental component associated with a virtual tissue processing and embedding station.
Figure 12A:
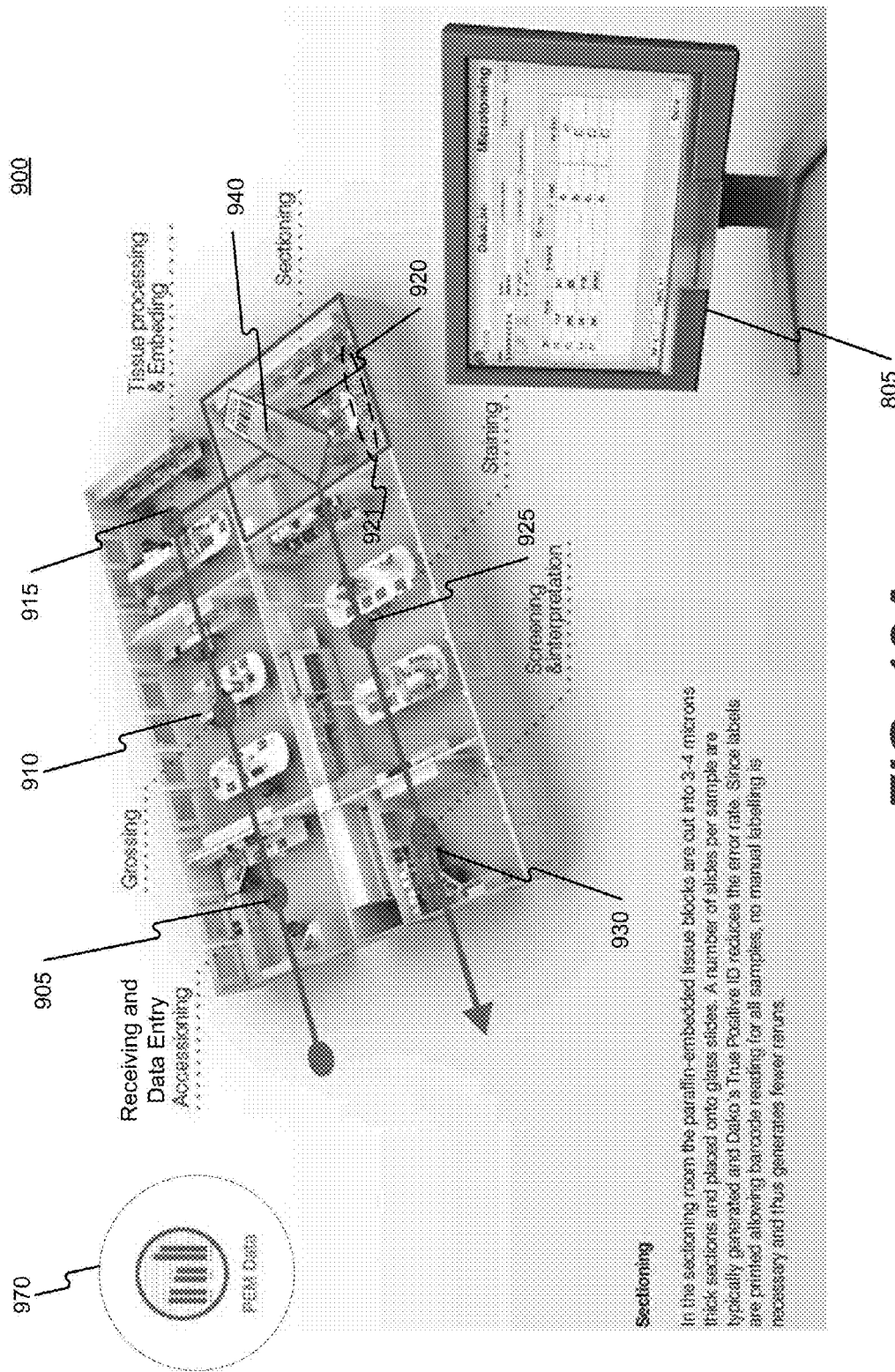
FIG. 12A is an exemplary depiction of a virtual laboratory following a user selection of a virtual sectioning station.
Figure 12B:
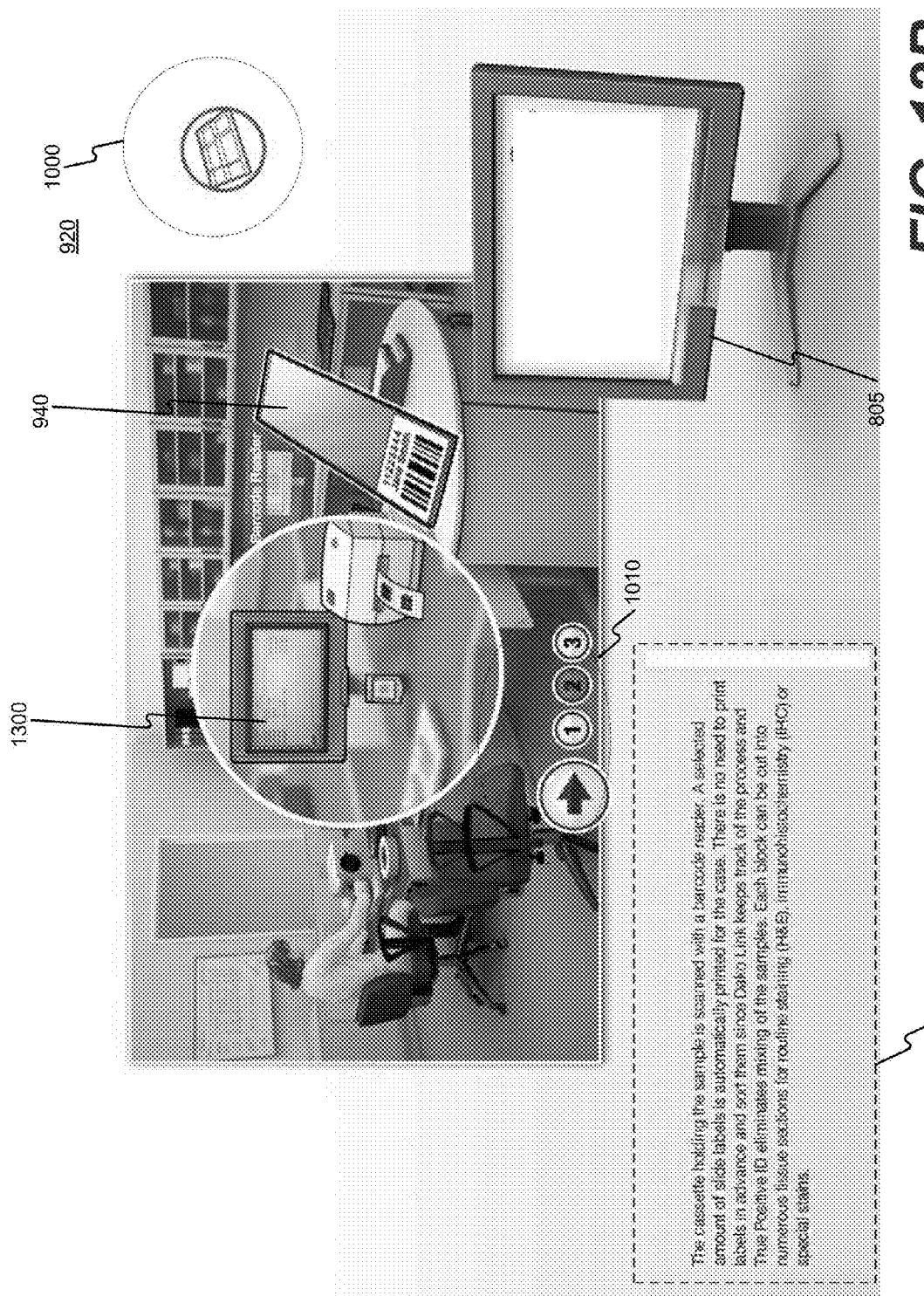
FIG. 12B is an exemplary representation of an interface providing a supplemental component associated with a virtual sectioning station.

FIG. 9B is an exemplary representation of an interface providing a supplemental component associated with virtual receiving and accessioning station 905 as modified in step 610. Such a supplemental component may include a detailed zoomed-in view of the virtual laboratory station selected including one or more virtual representations of laboratory devices present in the related physical laboratory (e.g., label printer, barcode reader, etc). Further, a supplemental component may include one or more additional active components 1010, a text component 1020, specimen indicator 940, and return component 1000, among other things. While supplemental component views may be discussed in the context of "zoomed-in" and "detailed," additional visual effects may be utilized for providing such components.

Return component 1000 may allow a user selection indicating a return to a view level above the currently selected view. For example, where a user has selected an active component indicating a drilldown view of a virtual laboratory station from virtual laboratory 900, return component 1000 may cause interface modules 201 to return to a view of virtual laboratory 900 within an interface. Similarly, where a user has drilled down two levels to a supplemental view of a supplemental component view of a laboratory workstation, return component 1000 may allow the user to return to the first supplemental component view of the laboratory workstation.

Specimen indicator 940 in a supplemental component view may be configured to provide information related to a theoretical current state of a specimen in the selected virtual laboratory station. For example, as noted above specimens arriving to receiving and accessioning stations 105 and 110, may be in jars and may be accompanied by a request form indicating desired tests for the specimen. As shown in FIG. 9B, such a state may be indicated by specimen indicator 940. In addition, various effects may be utilized with regard to specimen indicator 940 to assist in demonstrating a workflow. For example, within a supplement component view such as that shown in FIG. 9B, specimen indicator may become animated to demonstrate motion through the virtual laboratory station, among other things.

Figure 13A:
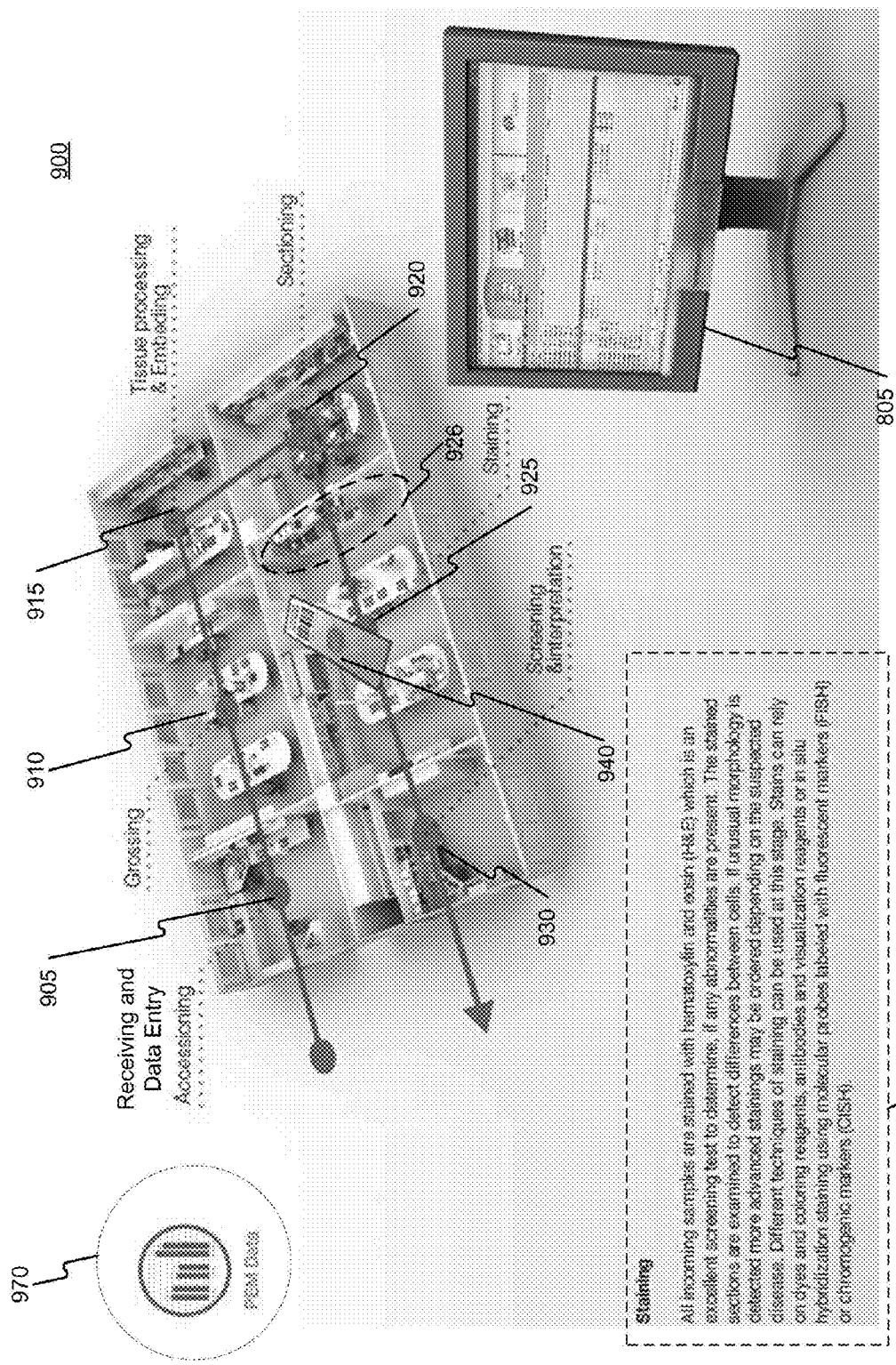
FIG. 13A is an exemplary depiction of a virtual laboratory following a user selection of virtual staining station.
Figure 13B:
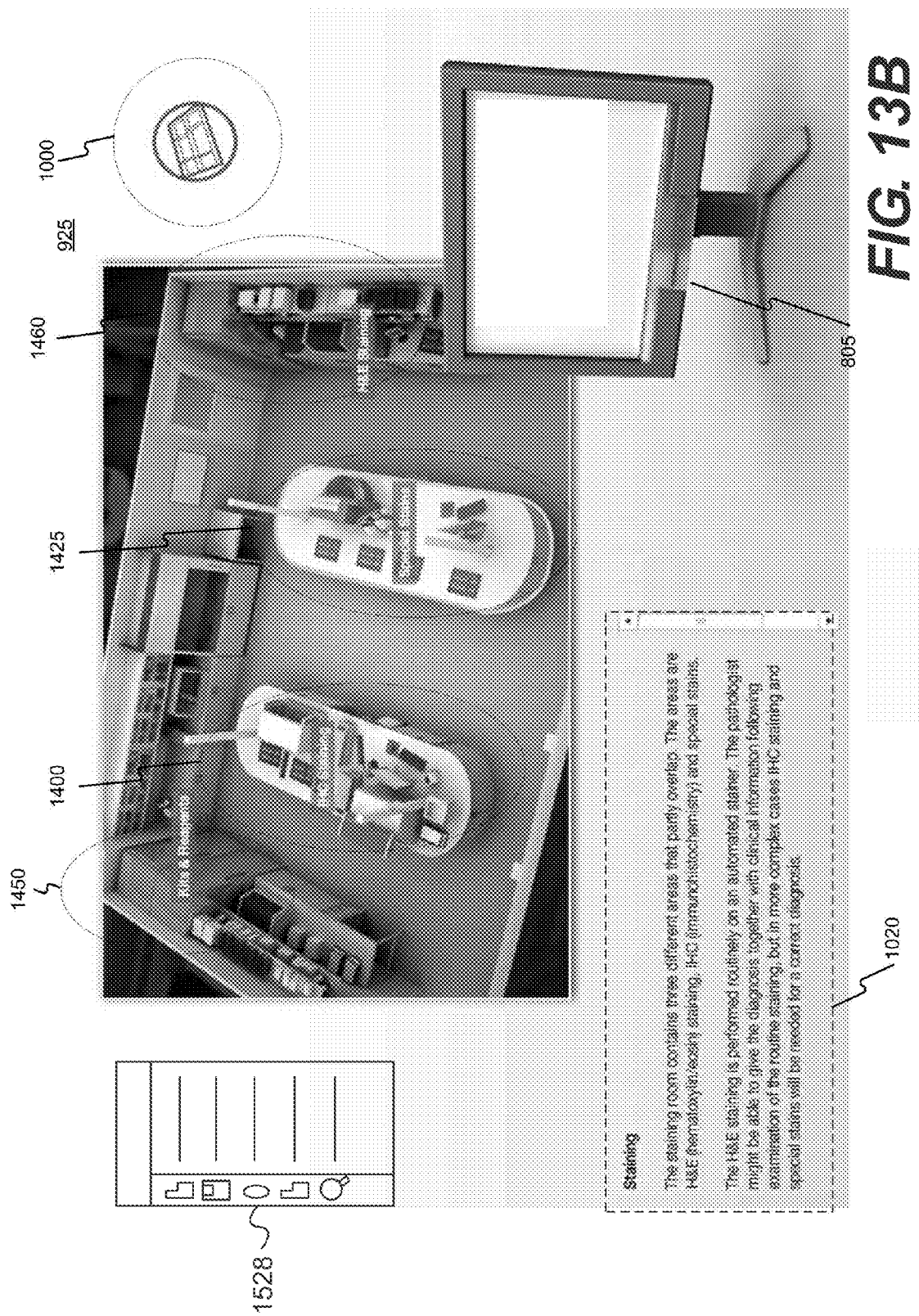
FIG. 13B is an exemplary representation of an interface providing a supplemental component associated with virtual staining station where additional drilldown is available.

A virtual laboratory station may also have one or more active components enabling a user to select one or more distinct supplemental components associated with a supplemental component virtual laboratory station. For example, FIGS. 13A-13C show an exemplary virtual staining station 925. As shown in FIG. 6, upon selecting virtual staining station 925 (step 605), a user may be presented with a supplemental component view (FIG. 13B) providing multiple active components 1400-1460 allowing user selection of a supplemental view of a virtual H&E staining station, a virtual advanced staining station, a virtual special staining station, and kits and reagents, among others (step 610). Because additional drilldown options may be available from this laboratory station component (step 615: yes), a user may again make a selection of another active components (e.g., active components 1400-1460) (step 605). Upon selection of an additional active component (e.g., 1425), a user may again drilldown to a supplemental component view of a laboratory station (e.g., H&E staining station 1430 as shown in FIG. 13C) (step 610). Once drilled down to a desired level, (step 615:no) a user may continue to step 620. One of skill in the art will recognize upon review of the present disclosure that numerous other configurations are possible. For example, prior to reaching a desired level associated with a laboratory station, selections may be available to allow a user to view information associated with higher level components.

Once a desired supplemental component has been reached, information related to that supplemental component may be displayed as well as additional active components 1010, which may enable another user selection related to the supplemental component view associated with a virtual laboratory station (step 620). As described above, a specimen may undergo one or more processes at each physical lab station. Where such additional information related to a laboratory station is available, additional active components 1010 may include a collection of active components configured to enable a user selection with regard to a predetermined number of processing stages associated with the selected laboratory station (step 625:yes). Upon receiving a user selection of an additional active component, specimen indicator may perform a visual indication of a process associated with the selection (e.g., move to a particular area of the station), and workflow server 155 may cause additional information related to the selected virtual laboratory station to be displayed at text component 1020 (step 630). Information displayed may include, for example, details of the process performed, laboratory devices utilized in the process, methods for improving the process, and any other desired information related to the selected laboratory station.

For example, as shown in FIG. 9B, additional active components 1010 may include an arrow component, and two numbered components (e.g., 1 and 2). Where a user desires to see a step by step of the workflow associated with the current laboratory station, and obtain related information to each step, the user may select the arrow component as desired, and each process in the current laboratory station may be displayed within the interface and described in text component 1020. Alternatively, if user wishes to review an individual process associated with the currently selected virtual laboratory station, the user may click one of the available numbered components (e.g., 1 and/or 2) to be taken directly to a data and description associated with the selected step.

Each virtual laboratory station may include one or more active components allowing receipt of a user selection in accordance with step 630. For examples related to each laboratory station, see FIGS. 9B, 10B, 11B, 12B, 13C, and 14B-C. Note that although exemplary active components are shown as sub-areas of each virtual laboratory station, active components may include the full virtual laboratory station area, or partial portions of a virtual laboratory station area.

Figure 14A:
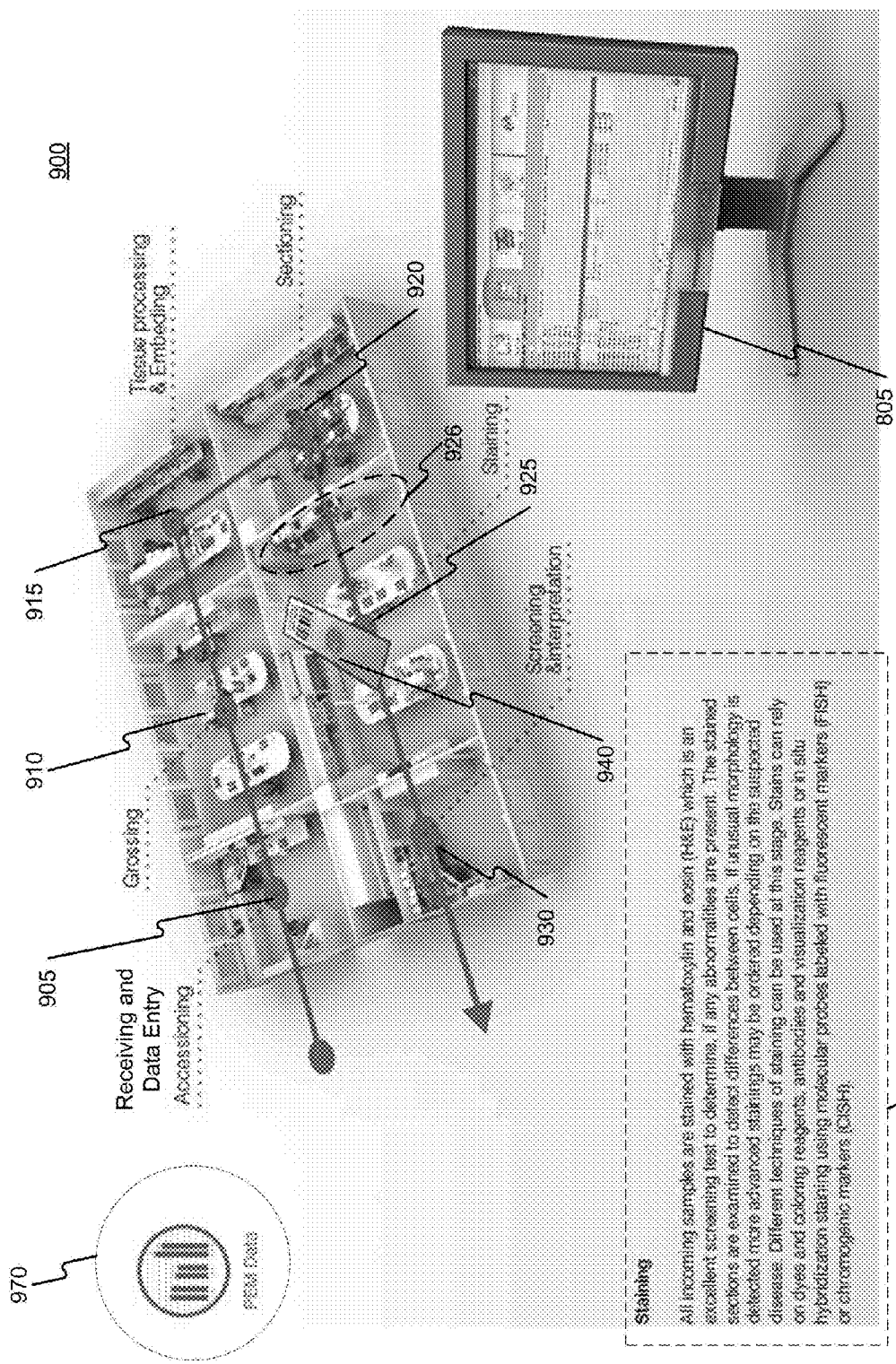
FIG. 14A is an exemplary depiction of a virtual laboratory following a user selection of a virtual imaging station.
Figure 14B:
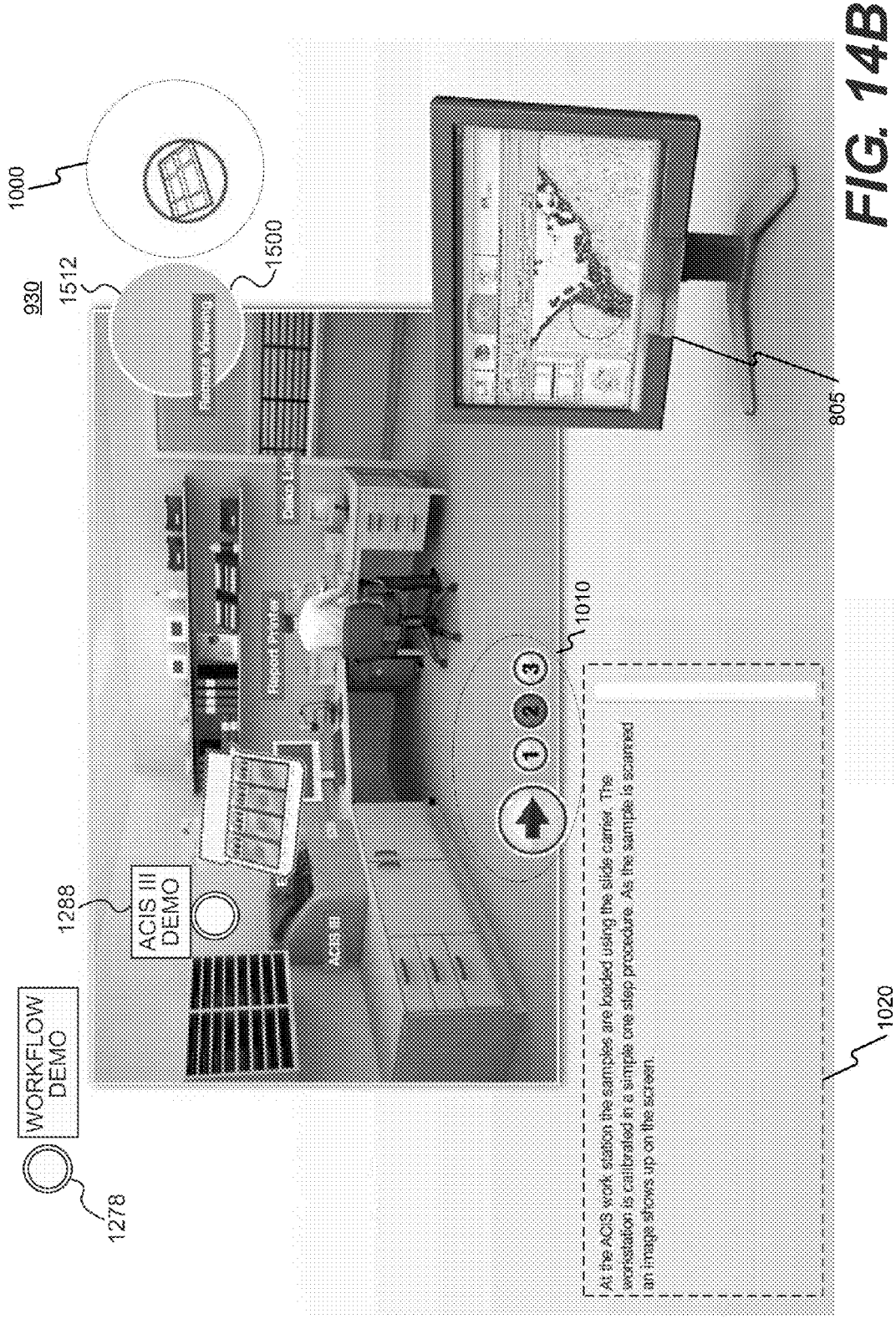
FIG. 14B is an exemplary representation of an interface providing a supplemental component associated with a virtual imaging station.
Figure 14C:
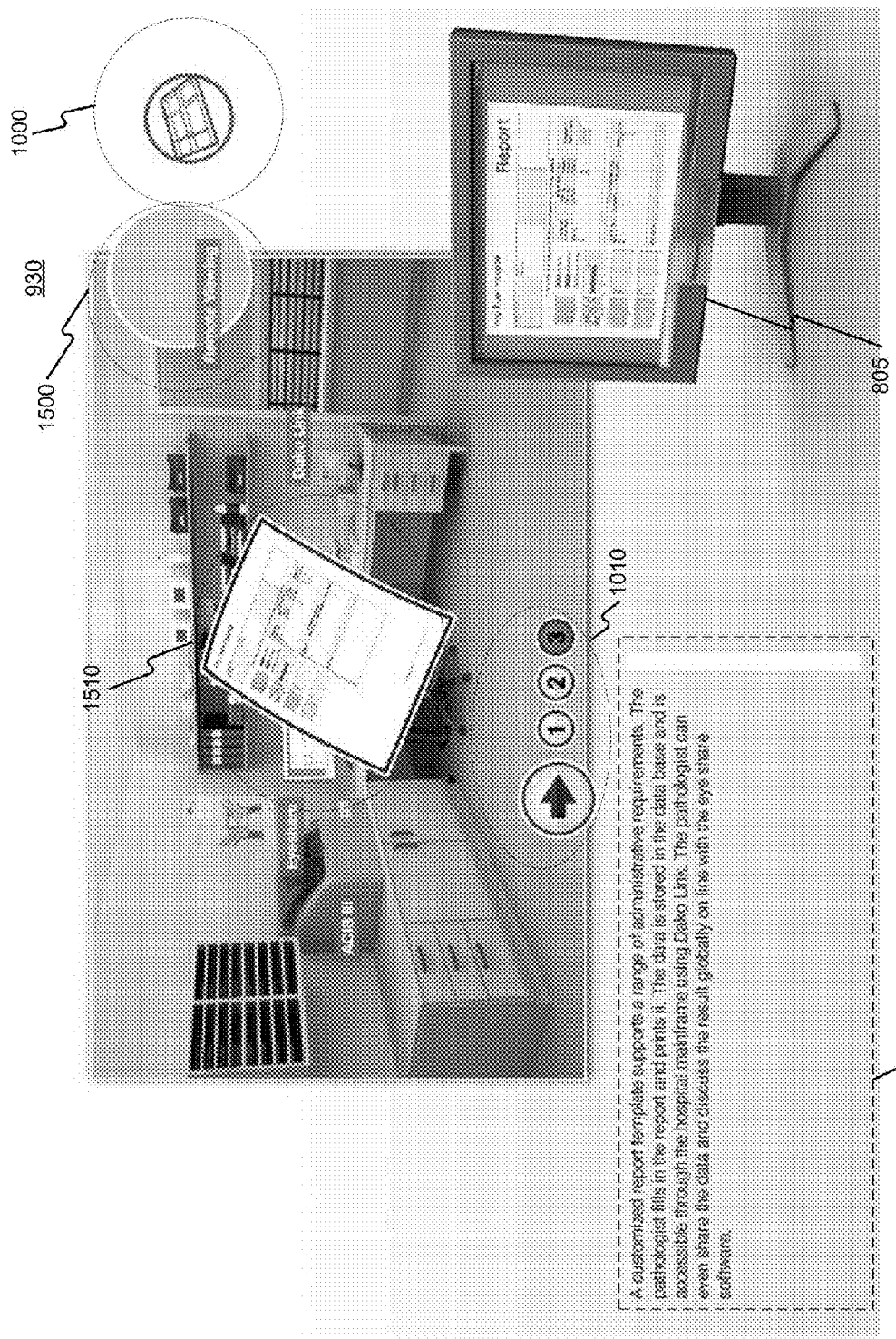
FIG. 14C is an exemplary representation of an interface providing additional functionality within a supplemental component associated with a virtual imaging station.

In some embodiments user selections may be enabled for viewing data associated with an actual physical specimen present in the selected virtual lab station. For example, FIGS. 14A-C depict views of an exemplary virtual imaging station 930. Image data associated with a specimen which has been imaged at imaging station 145, may be available for online viewing from within virtual imaging station 930. A user may therefore select specimen viewing component 1500 and may then be provided image and other data obtained at imaging station 125 related to a particular specimen. Similarly, a user may select to view a report for a particular specimen (e.g., including diagnosis/prognosis data). Where data for such a report is available (e.g., stored in workflow database 160), virtual lab station 930 may include specimen report component 1510. Upon selecting specimen report component 1510, a user may be provided a report, for example via analytical modules 203.

Similar functionality may be available at each virtual laboratory station associated with virtual laboratory 900, although not shown. For example, slide data associated with a physical specimen currently sectioned at sectioning station 125 may be available for online viewing from within virtual sectioning station 920. One of ordinary skill in the art will recognize that similar options may be available from within all virtual laboratory stations as desired.

Figure 15B:
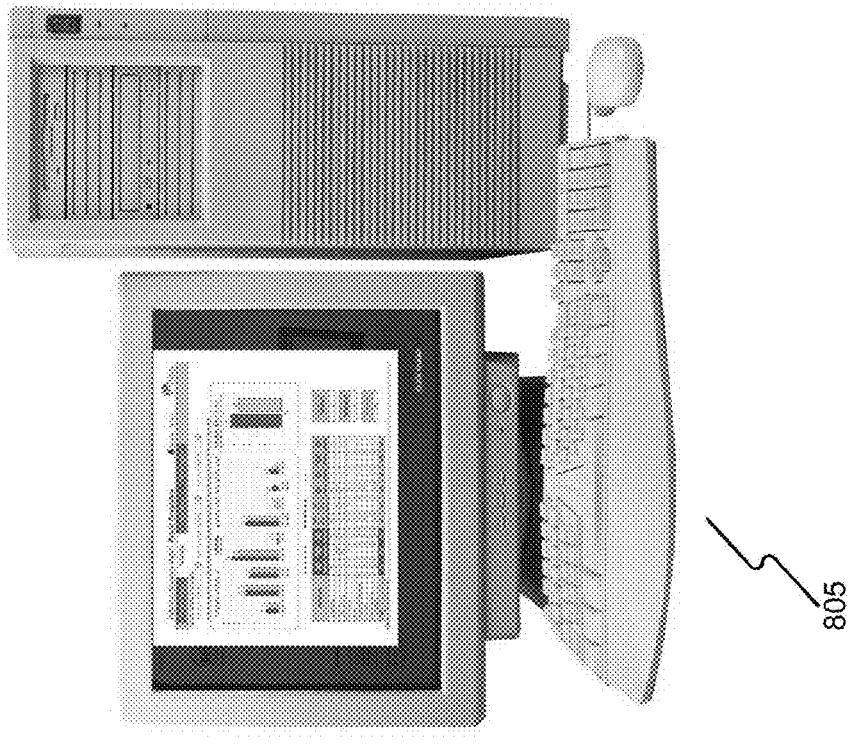
FIG. 15B is an exemplary depiction of a management workstation in data summary display mode following receipt of a user selection to view management and/or economic data.
Figure 15A:
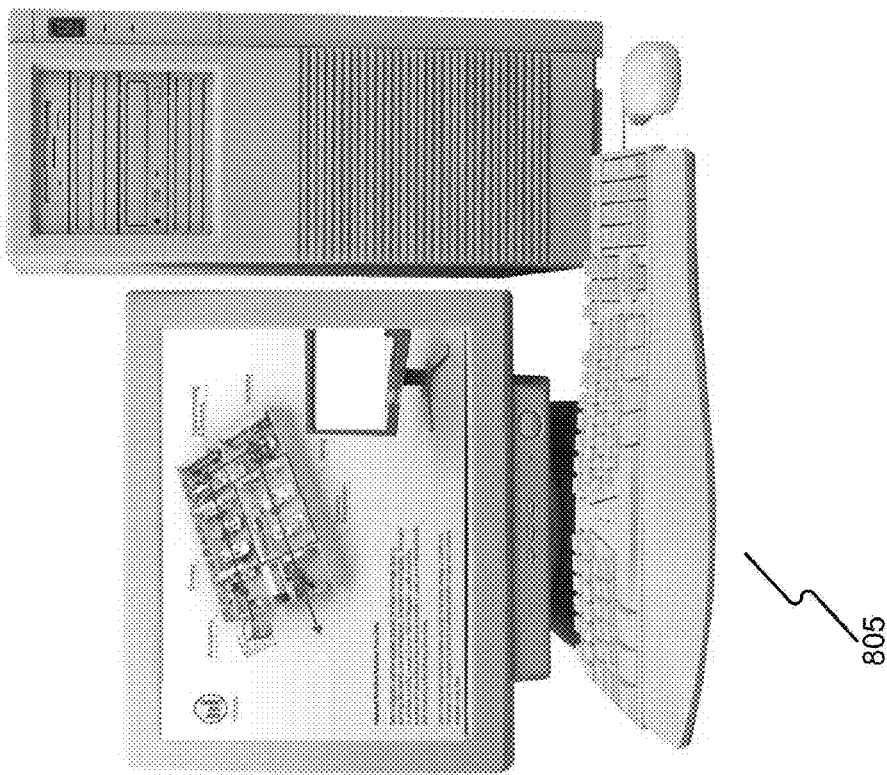
FIG. 15A is an exemplary depiction of a management workstation in virtual laboratory display mode.

Further, virtual laboratory stations 905-930 may be configured to demonstrate a workflow and workflow data associated with related physical laboratory stations using visual components and cues such as zoom-in effects, zoom-out effects, popup dialogs, drilldown effects, text cues, indicator arrows, and/or motion effects. FIG. 15A is an exemplary depiction of management workstation 805 in virtual laboratory display mode. For example, workflow indicator 960 may highlight a modeled workflow through virtual laboratory stations associated with virtual laboratory 900. Upon receiving a user selection of a virtual laboratory station (e.g., virtual imaging station 930), specimen indicator 940 may become animated and move in accord with the currently modeled workflow indicated by workflow indicator 960. As specimen indicator 940 follows workflow indicator 960 through each virtual laboratory station, specimen indicator 940 may change state based on a state at each virtual laboratory station. For example, where a user selects virtual imaging station 930, specimen indicator 940 may move into virtual receiving and accessioning station 905 and appear as a jar with request list. Specimen indicator 940 may pause there for a predetermined period and then move to virtual grossing station 910. At grossing station 910, specimen indicator 940 may change appearance to a labeled specimen cassette. Specimen indicator 940 may again pause, and then move to virtual tissue processing and embedding station 915, where its appearance may change to indicate a paraffinized specimen block on top of a labeled specimen cassette. Specimen indicator 940 may again pause, and then move to virtual sectioning station 920, where its appearance may change to indicate a labeled glass slide. Specimen indicator 940 may again pause, and then move to staining station 925, where its appearance may change to indicate a colored and labeled glass slide. Specimen indicator 940 may again pause, and then move to virtual imaging station 930, where its appearance may change to indicate a labeled printout or report of an imaged slide. More or fewer indications of workflow may occur based on a modeled workflow and administrator desires.

Virtual laboratory stations 905-930 may be configured to demonstrate supply data associated with physical laboratory stations. As shown in FIG. 13C, to demonstrate the supply data, virtual laboratory stations 905-930 may use a visual component and/or cue 1012 (e.g., zoom-in effects, zoom-out effects, popup dialogs, drilldown effects, text cues, indicator arrows, and/or motion effects). It is contemplated that the supply data may be represented textually (e.g., reagent level=30/35 mL) or graphically (e.g., using a chart, bar, meter, color, etc.). In one embodiment, a popup dialog 1014 may be associated with a particular laboratory device. For example, popup dialog 1014 may be associated with a stainer in virtual laboratory 900. Popup dialog 1014 may appear next to and indicate the reagent levels within the physical stainer using a bar graphic (i.e., height of bar changes as level of reagent changes). In another example, a refrigerator located in a virtual laboratory station may flash if the supplies contained in the physical refrigerator fall below a threshold. Specifically, the refrigerator may flash yellow if the supplies in the physical refrigerator fall below a first threshold, and the refrigerator may flash red if the supplies in the physical refrigerator fall below a second threshold. The laboratory devices located in virtual laboratory stations 905-930 may also include one or more active components 1016, which upon selection, allow a user to order more supplies in desired quantities. For example, the active component may link to a popup window with data entry fields usable for entering a quantity and/or type of a desired supply. The order for more supplies may be communicated via network 101 to a supply room or an outside vendor.

Virtual laboratory stations 905-930 may also be configured to allow control of one or more laboratory devices. In one embodiment shown in FIG. 13C, each laboratory device displayed in virtual laboratory stations 905-930 may include an active component 1018 that causes to appear or links to a control panel 1022 configured to control operation of the laboratory device. For example, an active component 1018 associated with virtual stainer located in virtual staining station 925 may link to a control panel 1022. Control panel 1022 may include one or more active components 1024 configured to control operation of a physical stainer located in a physical staining station. Alternatively, rather than linking to control panel 1022, active component 1018 may link to a separate application configured to operate the laboratory device (e.g., a stainer software). Selecting the active component associated with the laboratory device may cause a separate application to spawn in a new window (e.g., spawn in place of control panel 1022). This may allow the user to link to and run separate instrument specific applications that may not be integrated into virtual laboratory 900 (e.g., software packages from various manufacturers). It is contemplated that any application that can run in a window may be spawned in virtual laboratory 900 and/or virtual laboratory stations 905-930.

Virtual laboratory 900 and virtual laboratory stations 905-930 may be configured to display warning data related to a warning event. Warning data may be provided in any view of virtual laboratory 900, such as, for example, at a high level view of virtual laboratory 900 (e.g., FIG. 8), at a view highlighting one of virtual laboratory stations 905-930 (e.g., FIG. 9A), or at a supplemental view of a laboratory station 905-930 (e.g., FIG. 9B). Warning data may be provided using visual components and cues. As shown in FIG. 8, a visual component or cue 1138 (e.g., a popup dialog) 1138 may appear in virtual laboratory 900 and/or virtual laboratory stations 905-930 providing data regarding the source and nature of the warning event. Popup dialog 1138 may indicate, for example, that a laboratory device is being used outside of desired operating parameters or that a disruption in workflow is likely to occur. Warning events may include, for example, an incubation time running too long, expiration of a reagent in a stainer, a cassette printer running out of cassettes during a run, a power outage, a stainer cover being left open for too long, a temperature inside a stainer being outside of a desired range, and other warning events known in the art. For example, popup dialog 1138 may appear on virtual laboratory 900 and indicate that a temperature within a stainer in virtual staining station 925 is outside of a desired range. Popup dialog 1138 may also provide a link 1148 to virtual staining station 925. Selection of link 1148 may cause virtual staining station 925 to display. As seen in FIG. 13C, control panel 1022 may appear next to the stainer in virtual staining station 925, which includes one or more active components 1024 configured to control operation of the stainer (e.g., allows the user to shut down the stainer, discontinue the current staining operation, etc.). It is also contemplated that workflow server 155 may automatically control the laboratory device in order to remedy the cause of the warning. For example, workflow server 155 may automatically shut down the stainer if it detects that the stainer is running outside of desired operating conditions.

Virtual laboratory 900 and/or virtual laboratory stations 905-930 may be configured to display service information. At least some of the service information may be derived from sensors 102 associated with the laboratory devices. As shown in FIG. 8, in one embodiment of virtual laboratory 900 and/or virtual laboratory stations 905-930, a visual component and/or cue 1248 may display the service information (e.g., indicating a need for servicing of a particular physical laboratory device). Visual component or cue 1248 may be associated with one or more active components 1258 that allow an operator to take an action (e.g., request service from a technician, discontinue operation of the laboratory device, etc.). For example, when a laboratory device, such as a stainer, needs a diagnostic, a pop-up window 1268 may appear in virtual laboratory 900 and/or virtual laboratory stations 905-930 requesting authorization for a remote diagnostic of the stainer. A user may click on active element 1258 in pop-up window 1268 and provide authorization for the remote diagnostic. Virtual laboratory 900 and/or virtual laboratory stations 905-930 may also request user authorization to run automated servicing functions of the laboratory devices, such as auto-cleaning functions, software update functions, etc. It is contemplated that workflow server 155 may also automatically control the servicing of the laboratory devices. For example, workflow server 155 may automatically contact a technician to request servicing of a particular laboratory device. Workflow server 155 may request service upon detection of a service issue or upon a scheduled periodic basis.

It is contemplated that servicing status data and/or historical servicing data may be displayed in visual component and/or cue 1248 of virtual laboratory 900 and/or virtual laboratory stations 905-930. For example, a virtual laboratory station may display a last date of service, a status of a service request, a mean time between failure, and other service or service related information for one or more laboratory devices.

Virtual laboratory 900 and virtual laboratory stations 905-930 may include video functionality. As shown in FIG. 14B, virtual laboratory 900 and virtual laboratory stations 905-930 may include one or more active components 1278 that link to videos that demonstrate, for example, an exemplary workflow for a given virtual laboratory station. Virtual laboratory stations 905-930 may also include one or more active components 1278 that link to videos that provide an instructional demonstration of the workflow for a particular laboratory station. Additionally, virtual laboratory 900 and/or virtual laboratory stations 905-930 may include links 1288 to videos for specific laboratory devices (e.g., microscopes, stainers, barcode readers, printers, etc.). For example, a particular laboratory device may include an active component 1288 that links to an instructional video regarding operation of that laboratory device (e.g., instructional video regarding operation of a stainer). It is contemplated that the videos may be used for informational, training, and/or instructional purposes.

It is contemplated that virtual laboratory 900 and/or virtual laboratory stations 905-930 may include one or more active components 1512 that link to one or more cameras 103 (e.g., video cameras, still cameras) located in the physical laboratory (see FIG. 2). Cameras 103 may provide real-time video feedback from the physical laboratory. For example, an active component related to virtual grossing station 910 may link to and provide live video feedback from a camera 103 located in the physical grossing station. Each virtual laboratory station may link to a camera 103 that is located to observe the related physical laboratory station or stations. Virtual laboratory 900 and/or virtual laboratory stations 905-930 may also link to cameras 103 configured to observe a specific machine or operation. For example, virtual laboratory 900 and/or virtual laboratory stations 905-930 may link to a camera 103 that is configured to observe the sample as it passes through a staining operation.

Virtual laboratory 900, virtual laboratory stations 905-930, and the virtual laboratory devices contained therein may be flexible and allow for reconfiguration. In one embodiment shown in FIG. 13B, a user may select a reconfiguration mode from a menu 1528 associated with virtual laboratory 900. In reconfiguration mode, a user may be able to add or remove laboratory devices from virtual laboratory stations 905-930. For example, in a given virtual laboratory station, a user may be able to replace a high volume label printer with a series of smaller label printers (in order to accommodate a corresponding change in the physical laboratory). Similarly, a user may also be able to update a model of a virtual stainer in accordance with an updated model of a physical stainer. Additionally, a user may be able to perform one or more software updates for existing physical laboratory devices (i.e., update the software that operates a given laboratory device). One of ordinary skill in the art will recognize upon consideration of the present disclosure that virtual laboratory 900 may be configured to allow for numerous other types of updates and modifications, and those described herein are intended as exemplary.

Returning to FIG. 5, workflow server 155 may receive a request for an analysis of data associated with a physical laboratory represented by virtual laboratory 900 (e.g., from management workstation 805) (step 530:yes). FIG. 15B is an exemplary depiction of management workstation 805 in data summary display mode following receipt of a user selection to view management and/or economic data. Similar interfaces may be provided by workflow server at any desired location via network 101 or other suitable method.

Virtual laboratory 900 may include an analysis active component 970 enabling a selection by a user indicating a desire for management and/or economic data associated with a physical laboratory. Such information may include, for example, data related to at least one laboratory device, a job identifier, a time per operation, a user identifier, a success identifier, laboratory device service information, laboratory device status, physical laboratory economic data, lean workflow data, and/or potential improvement data. Such data may be provided by analytical modules 203, operational modules 202, and interface modules 201, via workflow server 155. It is also contemplated that external data may be provided via a connection of workflow server 155 to an outside network. For example, workflow server 155 may connect to outside servers configured to provide data from additional physical laboratories.

Figure 7:
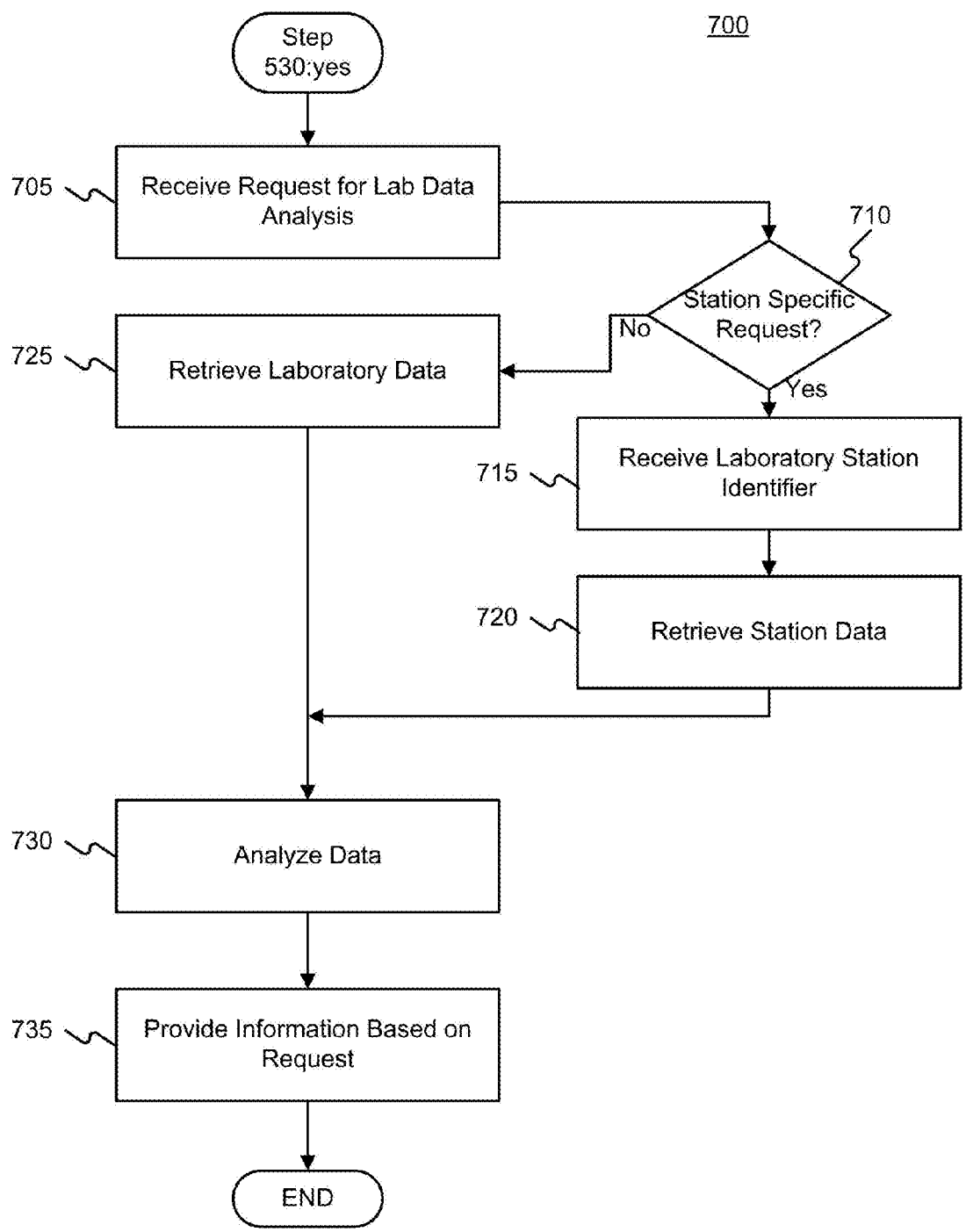
FIG. 7 is a block diagram of an exemplary method for providing work flow data associated with a physical laboratory.

FIG. 7 is a block diagram of an exemplary method for providing work flow data associated with a physical laboratory. Workflow server 155 may receive a request for laboratory data and/or data analysis (step 705). In some embodiments, data associated with individual laboratory stations may be accessed via management workstation 805. In such embodiments, when a particular laboratory station has been selected by a user, for example, using methods described above with reference to FIGS. 5 and 6, a laboratory station specific request may be initiated (step 710:yes). Upon receiving a selection for an analysis of data associated with a particular laboratory station a station ID may be determined based on a currently selected virtual laboratory station through virtual laboratory 900. For example, imaging station 145 and virtual imaging station 930 may be linked via a station ID in workflow database 160. Upon determining that virtual imaging station 930 has been selected by user and a subsequent request for data initiated, analytical modules 203 may retrieve data from workflow database 160 according to the ID associated with imaging station 145 and virtual imaging station 130 (step 720).

Alternatively, a user may wish to view a broader dataset associated with a physical laboratory. In such an example, a request for data may be received where a user has not selected a particular laboratory station from virtual laboratory 900 (step 710:no). Therefore, analytical modules 203 may retrieve data from workflow database 160 for the entire physical lab (step 725).

Retrieved data may be processed using various data analysis algorithms provided with analytical modules 203 (step 730). For example, analysis may be performed on laboratory station specific workflow data to provide results related to operator efficiency, machine efficiency, and average cost per operation at a particular laboratory station. In another example data associated with a physical laboratory may be analyzed to provide an executive summary of operational efficiency through the physical laboratory. Numerous other results may be obtained through analysis of workflow data related to a physical laboratory. For example, operational times for a laboratory or laboratory station may be averaged over a time period (e.g., a year), operator downtime may be determined, success rates by operator and station may be obtained, and errors may be analyzed on a station and laboratory basis, among other things.

Following analysis of workflow data according a user request, workflow server 155 may provide the analyzed data to the user according to the user's selections (step 735). Workflow server may utilize interface modules 201 and data analytical modules 203, among other things, for providing the analyzed data to a user.

FIGS. 15C-H are depictions of exemplary report interface 1600 for providing analyzed data to a user consistent with embodiments of the present disclosure. Report interface 1600 may include report selector group 1605. Report selector group may include one or more active components enabling receipt of a user selection. Such a user selection may relate to a type of data a user wishes to see and/or how the user wishes to view the data (e.g., what type of report). For example, data may be represented in tabular, chart, or other suitable form.

Figure 15C:
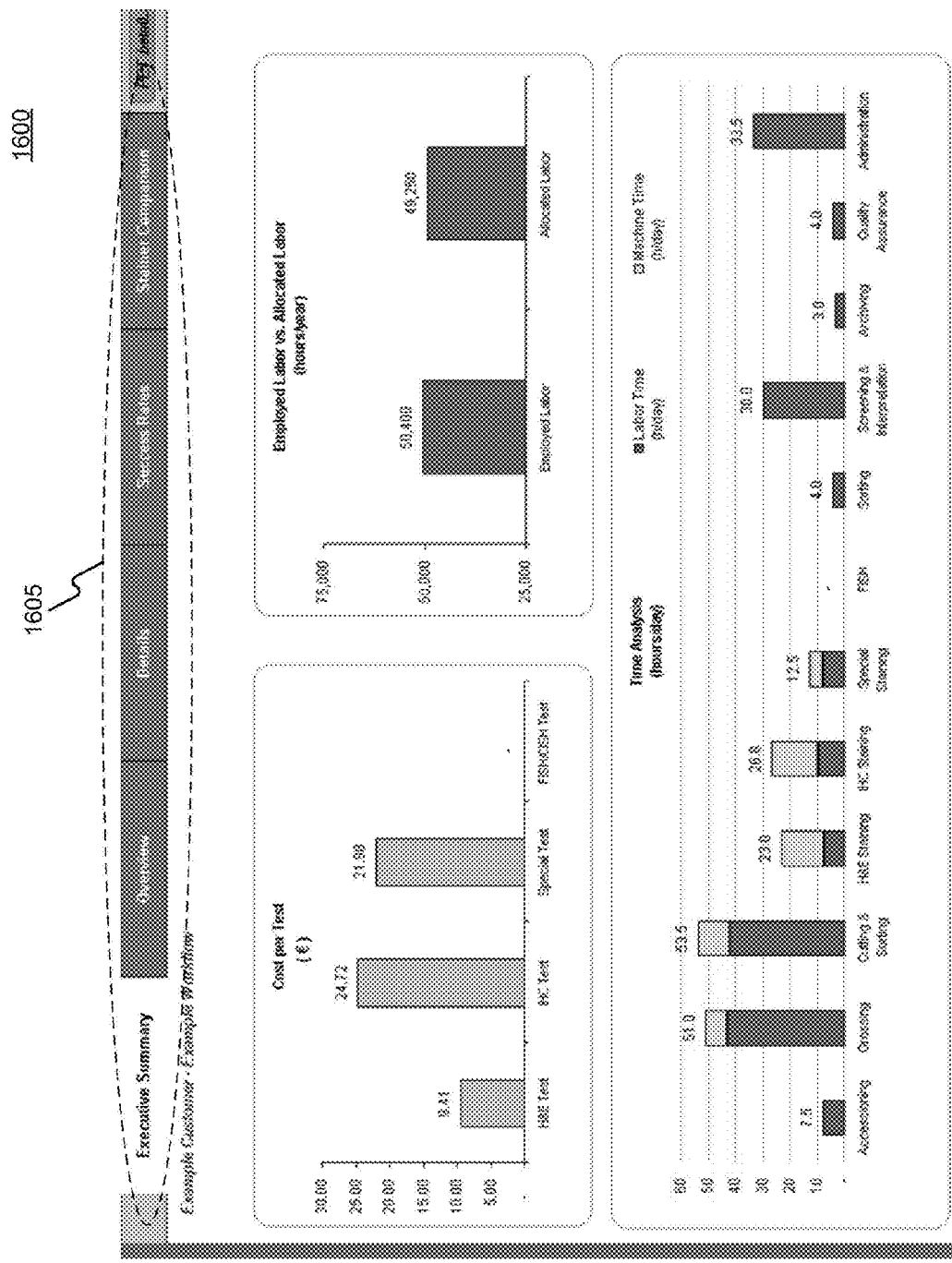
FIG. 15C is a depiction of an exemplary report interface for providing analyzed data to a user consistent with embodiments of the present disclosure.
Figure 15D:
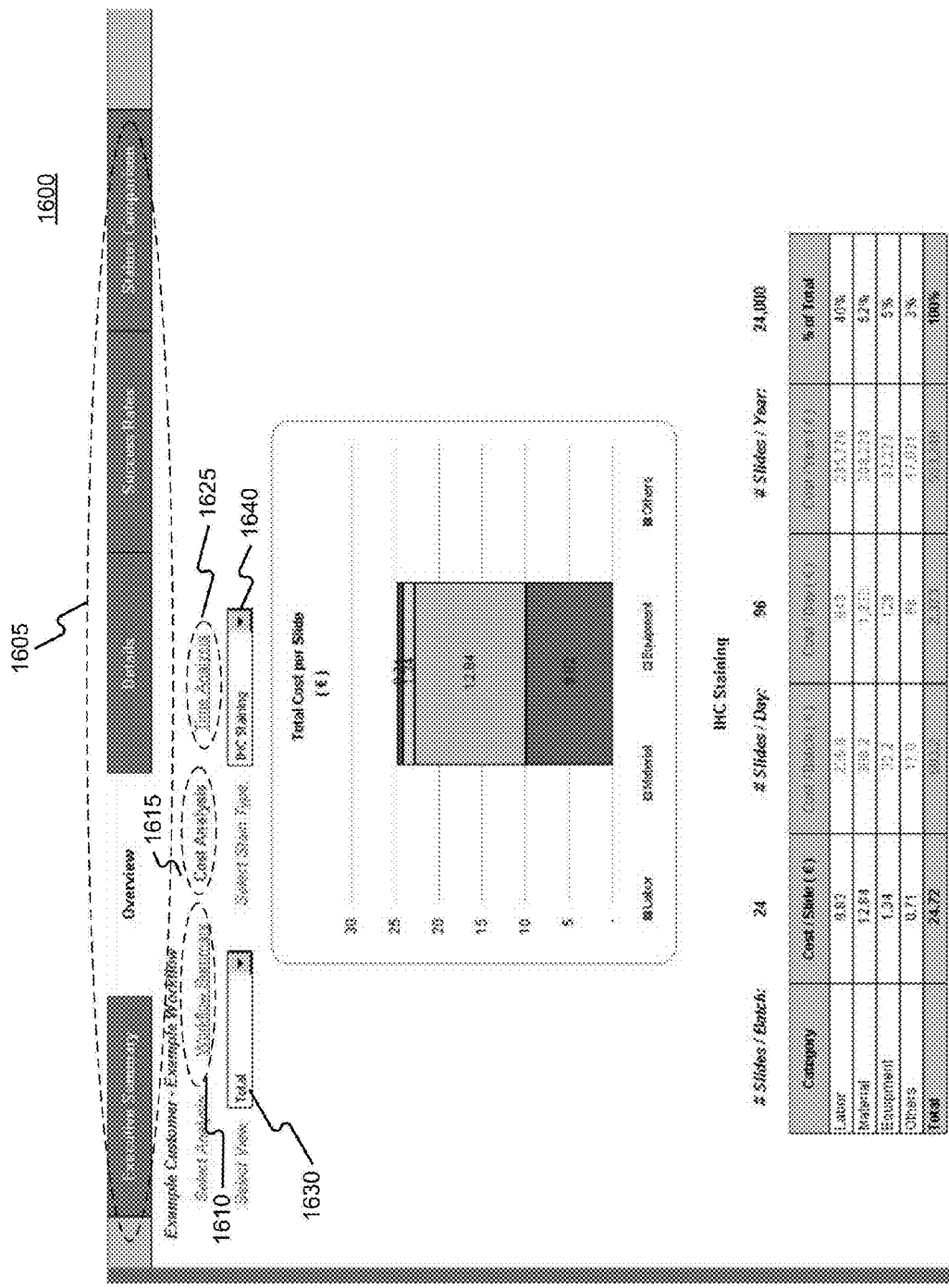
FIG. 15D is another depiction of an exemplary report interface for providing analyzed data to a user consistent with embodiments of the present disclosure.

FIG. 15C is an exemplary executive summary report. Such a report may include data such as, for example, cost per laboratory test, labor hour data, and time analyses. Utilizing active components associated with report selector group 1605, a user may select another type of report interface such as an example workflow overview as shown at FIG. 15D. Such an interface may include additional active components enabling receipt of additional user selections. Analysis selectors 1610-1625 may allow a user to change the type of analysis performed at step 730. For example, a user may select to analyze data based on workflow, cost, and/or time, among others. Upon such a selection, workflow server 155 may access analytical modules 203 for providing the analysis requested by the user and interface modules 201 to provide report interface 1600.

Additional active components may also be provided, including for example, pushbuttons, dropdown lists, radio buttons, etc. As shown in FIG. 15D, dropdown components 1630 and 1640 may enable a user to further customize data displayed in report interface 1600.

Figure 15E:
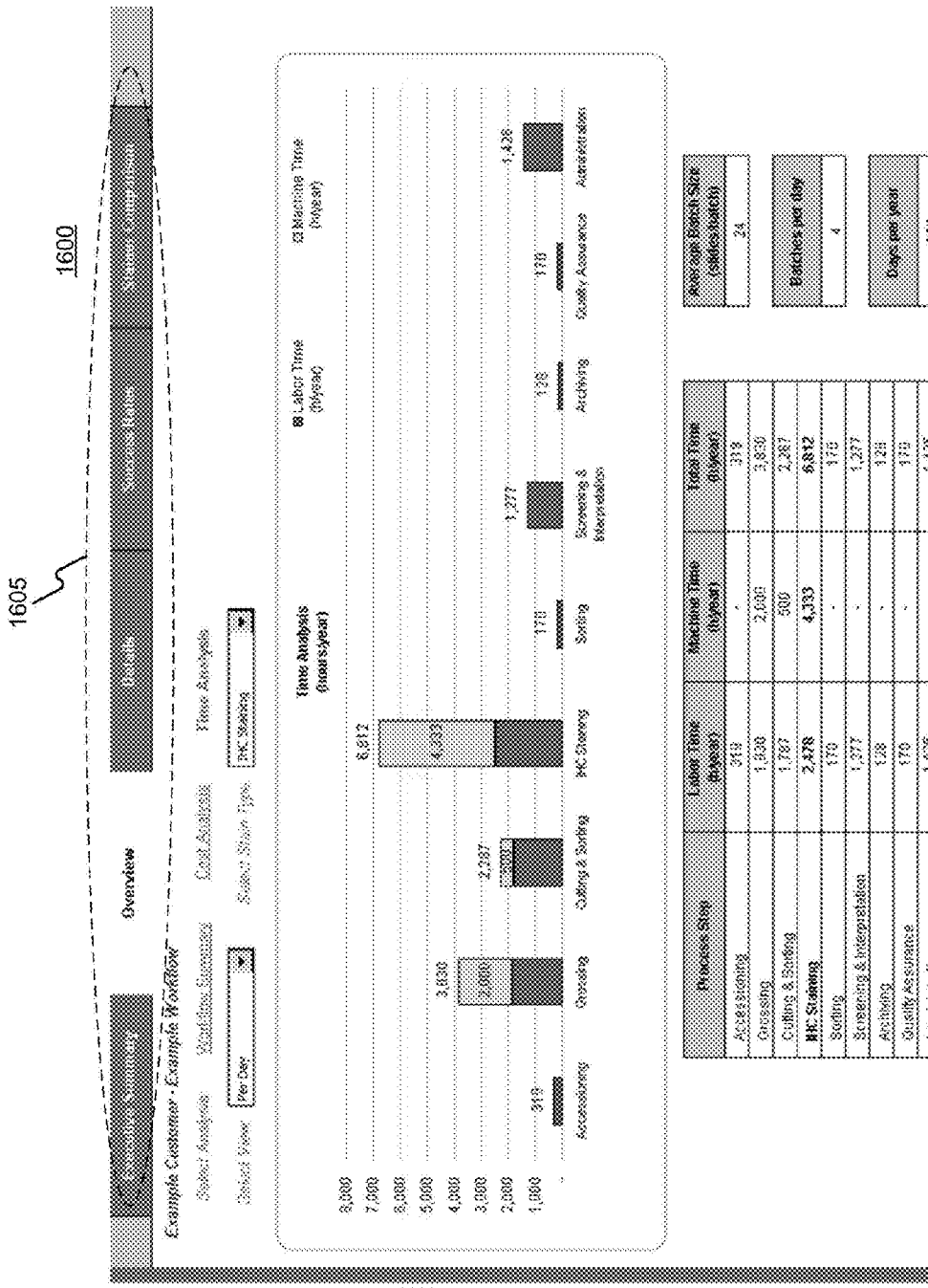
FIG. 15E is yet another depiction of an exemplary report interface for providing analyzed data to a user consistent with embodiments of the present disclosure.
Figure 15F:
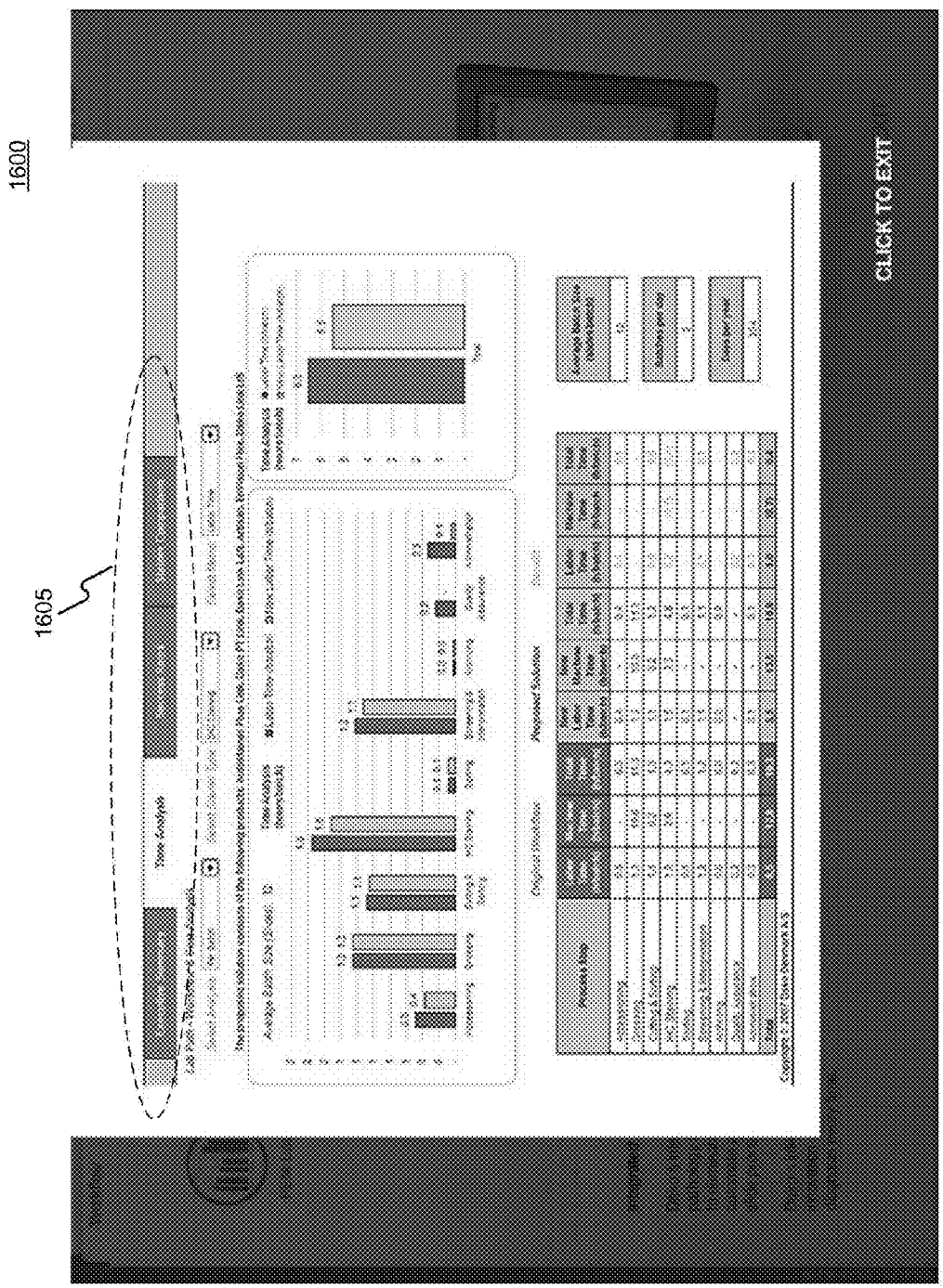
FIG. 15F is yet another depiction of an exemplary report interface for providing analyzed data to a user consistent with embodiments of the present disclosure.
Figure 15G:
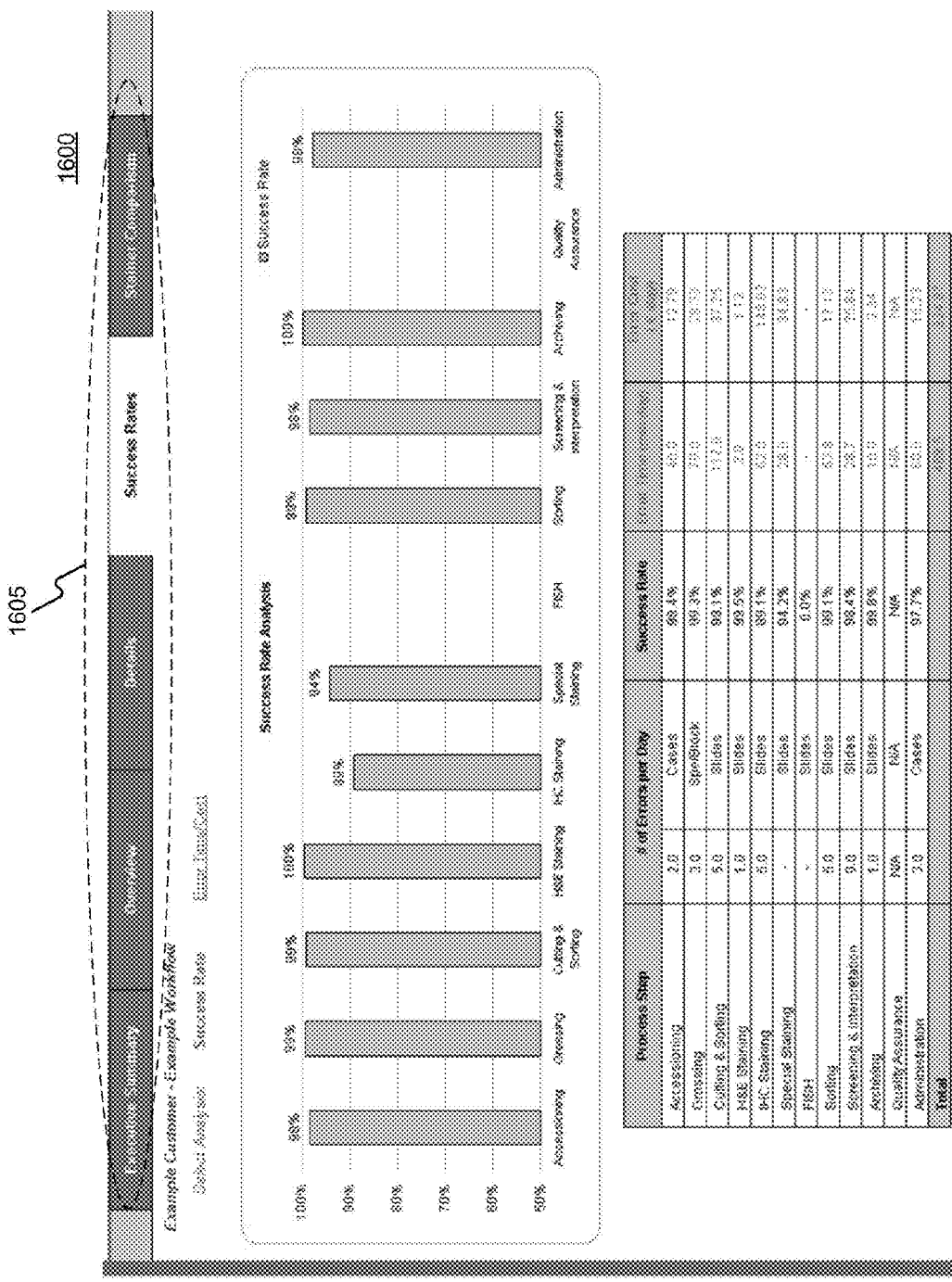
FIG. 15G is yet another depiction of an exemplary report interface for providing analyzed data to a user consistent with embodiments of the present disclosure.
Figure 15H:
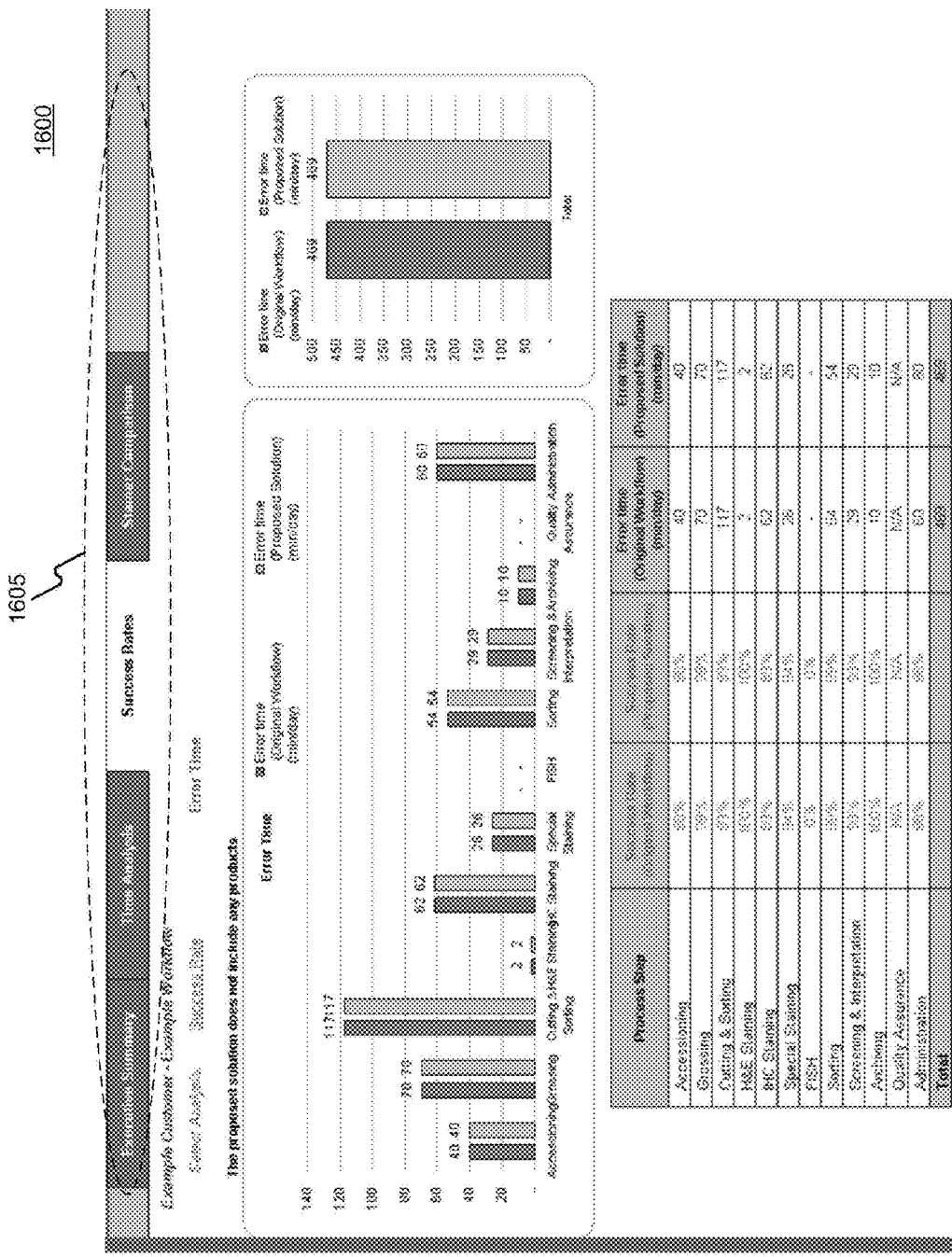
FIG. 15H is yet another depiction of an exemplary report interface for providing analyzed data to a user consistent with embodiments of the present disclosure.

FIGS. 15D-F are depictions of exemplary report interfaces 1600 analyzing various laboratory workflow data based varying user selections. FIGS. 15G and H are depictions of an exemplary report interfaces 1600 analyzing success rates and errors within a laboratory.

Report interface 1600 may also include reports comparing the performance of one or more physical labs, laboratory stations, or laboratory devices to industry standards. In one embodiment, workflow server 155 may be configured to receive industry standard data which is used by report interface 1600 to create a comparative report. For example, the comparative report may display operator efficiency data, machine efficiency data, cost per operation data, time per operation data, success rate per time period data, etc. as compared to corresponding industry standard data. It is contemplated that the industry standard data may be received directly from competitors, from a third party vendor, or from any other source. The industry standard data may be an average of competitors in the industry or, when available, data related to a specific competitor.

Report interface 1600 may also include one or more reports displaying quality control information. For example, a quality control report may include information on usage of a laboratory device during a given time period, a process control diagram, mean time between failures information, and other quality control information known in the art. The quality control report may include incidents related to specific laboratory devices that resulted in warnings. The quality control report may include the date of the warnings, the nature of the warnings, the severity of the warnings, and other related information. The quality control report may also display trend data related to quality control for the entire lab, one or more laboratory stations, or one or more laboratory devices over a given period of time.

Upon exiting report interface 1600, GUI module 205 may return the modify a display to once again show virtual laboratory interface 900 (as shown in FIG. 15A), or any other suitable interface may be provided (step 540).

One of ordinary skill in the art will recognize upon consideration of the present disclosure that many methods maybe used for analyzing, customizing, and providing laboratory workflow data to a user. Therefore, those methods described herein are not intended to be limiting.

Utilizing systems and methods of the present disclosure it may be possible to model, visualize, and analyze workflows associated with a physical laboratory. By enabling such modeling, visualization, and analysis, improvements may be made to previously existing laboratory workflows and cost savings, among other things, may be realized. Further, systems and methods of the present disclosure may be utilized as a training tool and/or a sales tool for demonstrating workflow, and potential improvements to efficiency and reductions in cost through modifications to laboratory workflow.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A tangible non-transitory computer-readable storage device storing computer-executable program instructions that generate a user interface for displaying workflow information associated with a tissue specimen in a pathology laboratory, the program instructions performing a method comprising:
   displaying a virtual laboratory component providing a graphical representation that depicts an appearance and physical layout of a physical pathology laboratory, the virtual laboratory component having one or more virtual laboratory stations graphically representative of one or more corresponding physical laboratory stations for processing the tissue specimen, wherein relative positions of the virtual laboratory components reflect relative positions of the corresponding physical laboratory stations, and wherein the tissue specimen is processed by the one or more physical laboratory stations according to a workflow;
   displaying a specimen indicator that indicates a current specimen state based on a current relationship of the tissue specimen to the workflow;
   wherein the one or more virtual laboratory stations include at least one of a tissue specimen receiving station, a tissue specimen grossing station, a tissue specimen processing station, a tissue specimen embedding station, a tissue specimen sectioning station, a tissue specimen staining station, a tissue specimen imaging station, a tissue specimen archiving station, or a tissue specimen image archiving station,
   enabling a first active component associated with the virtual laboratory component, wherein the first active component is configured to receive a user selection of a virtual laboratory station graphically representative of a corresponding physical laboratory station; and
   generating a supplemental view component of the selected virtual laboratory station in response to the user selection, wherein the supplemental view provides supplemental information on processing of the tissue specimen by the corresponding physical laboratory station graphically represented by the selected virtual laboratory station.

2. The computer-readable storage device of claim 1, wherein the current specimen state indicated by the specimen indicator is at least one of a container, a cassette or a slide.

3. A computer-implemented method for generating a user interface to display workflow information associated with a specimen in a laboratory, the method comprising:
   displaying a virtual laboratory component providing a graphical representation that depicts an appearance and physical layout of a physical laboratory, the virtual laboratory component having one or more virtual laboratory stations graphically representative of one or more corresponding physical laboratory stations, wherein relative positions of the virtual laboratory components reflect relative positions of the corresponding physical laboratory stations;
   displaying a specimen indicator in relation to the one or more virtual laboratory stations, indicating a specimen location in relation to one or more physical laboratory stations corresponding to the one or more virtual laboratory stations;
   wherein the one or more virtual laboratory stations include at least one of a tissue specimen receiving station, a tissue specimen grossing station, a tissue specimen processing station, a tissue specimen embedding station, a tissue specimen sectioning station, a tissue specimen staining station, a tissue specimen imaging station, a tissue specimen archiving station, or a tissue specimen image archiving station,
   enabling, via a processor, a first active component associated with the virtual laboratory component, wherein the first active component is configured to receive a user selection of a virtual laboratory station included in the virtual laboratory component; and
   generating a supplemental view component of the selected virtual laboratory station graphically representative of the corresponding physical laboratory station in response to the user selection.

4. The method of claim 3, wherein the supplemental view component includes a second active component configured to receive a second user selection, wherein the second active component indicates a predetermined number of processing stages associated with the selected second virtual laboratory station graphically representative of a corresponding second physical laboratory station.

5. The method of claim 3, wherein the virtual laboratory component is configured to display a visual indicator of the workflow.

6. The method of claim 5, wherein the visual indicator includes at least one of a zoom-in effect, a zoom-out effect, a popup dialog, a drilldown effect, a text cue, an arrow, or a motion effect.

7. The method of claim 3, further comprising automatically moving the specimen location indicator to demonstrate a current position of the specimen in the workflow.

8. The method of claim 5, further comprising displaying a specimen type indicator configured to indicate a specimen type in relation to the workflow.

9. The method of claim 4, further comprising displaying a text component having information related to the selected virtual laboratory station based on the first or second user selection.

10. The method of claim 8, wherein the information of the text component includes text describing a process executed at the physical laboratory station represented by the selected virtual laboratory station.

11. The method of claim 4, further comprising providing a third active component enabling a third user selection to review management data associated with the physical laboratory.

12. The method of claim 11, wherein the management data includes at least one of a specimen status and a specimen image associated with the specimen.

13. The method of claim 3, wherein the virtual laboratory includes an indication of a complete workflow through the physical laboratory.

14. A tangible non-transitory computer-readable storage device storing computer-executable program instructions that generate a user interface, for displaying workflow information associated with a specimen in a laboratory, the interface comprising:
   a virtual laboratory component providing a graphical representation that depicts an appearance and physical layout of the physical laboratory, the virtual laboratory component having one or more virtual laboratory stations graphically representative of one or more corresponding physical laboratory stations, wherein relative positions of the virtual laboratory components reflect relative positions of the corresponding physical laboratory stations;

a display component displaying a specimen indicator that indicates a current specimen state based on a current relationship of the tissue specimen to the workflow;

wherein the one or more virtual laboratory stations include at least one of a tissue specimen receiving station, a tissue specimen grossing station, a tissue specimen processing station, a tissue specimen embedding station, a tissue specimen sectioning station, a tissue specimen staining station, a tissue specimen imaging station, a tissue specimen archiving station, or a tissue specimen image archiving station, a first active component associated with the virtual laboratory component, wherein the first active component is configured to receive a user selection of a virtual laboratory station included in the virtual laboratory component;

and a supplemental view component of the selected laboratory station, wherein the supplemental view component is displayed in response to the user selection.

15. A method for providing workflow information associated with processing of specimens in a physical laboratory, the method comprising:

storing device data associated with a laboratory device in the physical laboratory;

displaying a virtual laboratory component providing a graphical representation that depicts an appearance and physical layout of the physical laboratory, the virtual laboratory component having one or more virtual laboratory stations graphically representative of one or more corresponding physical laboratory stations, wherein relative positions of the virtual laboratory components reflect relative positions of the corresponding physical laboratory stations;

displaying a specimen indicator that indicates a current specimen state based on a current relationship of the tissue specimen to the workflow;

wherein the one or more virtual laboratory stations include at least one of a tissue specimen receiving station, a tissue specimen grossing station, a tissue specimen processing station, a tissue specimen embedding station, a tissue specimen sectioning station, a tissue specimen staining station, a tissue specimen imaging station, a tissue specimen archiving station, or a tissue specimen image archiving station, enabling, via a processor, a first active component associated with the virtual laboratory component, wherein the first active component is configured to receive a user request for workflow information associated with a selected virtual laboratory station graphically representative of a corresponding physical laboratory station;

generating a supplemental view component of the selected virtual laboratory station graphically representative of the corresponding physical laboratory station in response to the user selection;

processing, based on the request, the device data to generate the workflow information; and providing the workflow information to the user.

16. The method of claim 15, wherein the information is provided within the context of the one or more virtual laboratory stations.

17. The method of claim 15, wherein the data related to at least one laboratory device includes a job identifier, a time per operation, a user identifier, and a success identifier.

18. The method of claim 15, wherein the information relates to at least one of laboratory device service information, laboratory device status, physical laboratory economic data, lean workflow data, and potential improvement data.

19. The method of claim 15, wherein the information includes at least one of an average labor time, an average machine time, a success rate, and a cost.

20. The method of claim 19, further comprising enabling modification of the workflow to generate modified information, the modified information including at least one of an estimated labor time, an estimated machine time, an estimated success rate, and an estimated cost.

21. The method of claim 20, further comprising comparing the information with the modified information.

22. The method of claim 15, wherein the information includes an economic summary related to the physical laboratory.

23. The method of claim 15, wherein the receiving step includes at least one of receiving a click event from an active component and receiving a text based request.

24. The method of claim 15, further comprising:
modeling the workflow in a virtual laboratory diagram as a first result;
receiving information related to a proposed workflow associated with the physical laboratory;
modeling the proposed workflow in the virtual laboratory diagram as a second result;
comparing the first result and the second result; and
providing a summary based on the comparison.

25. The method of claim 24, wherein the information related to a proposed workflow includes information related to addition of a laboratory device.

26. A system for providing data related to a physical laboratory, the system comprising:
a workflow server configured to receive data related to a physical laboratory;
a laboratory device in communication with the workflow server and configured to provide the data;
a display device; and
an interface component configured to:
display a virtual laboratory component providing a graphical representation that depicts an appearance and physical layout of the physical laboratory, the virtual laboratory component having one or more virtual laboratory stations graphically representative of one or more corresponding physical laboratory stations, wherein relative positions of the virtual laboratory components reflect relative positions of the corresponding physical laboratory stations;
displaying a specimen indicator that indicates a current specimen state based on a current relationship of the tissue specimen to the workflow;
enable a first active component associated with the virtual laboratory component, wherein the first active component is configured to receive a user request for workflow information associated with a selected virtual laboratory station graphically representative of a corresponding physical laboratory station;
wherein the one or more virtual laboratory stations include at least one of a tissue specimen receiving station, a tissue specimen grossing station, a tissue specimen processing station, a tissue specimen embedding station, a tissue specimen sectioning station, a tissue specimen staining station, a tissue specimen imaging station, a tissue specimen archiving station, or a tissue specimen image archiving station,
generate a supplemental view component of the selected virtual laboratory station graphically representative of the corresponding physical laboratory station in response to the user selection;
process, based on the request, the device data to generate the workflow information; and
provide the workflow information to the user.

27. The system of claim 26, wherein the laboratory device includes at least one of a staining machine, a microtome, a microscope, a cassette printer, a hybridizer, and a specimen barcode reader.

28. The system of claim 26, further comprising a database in communication with the workflow server and configured to store the data.

29. The system of claim 26, wherein the output includes at least one of an average labor time, an average machine time, a success rate, a cost, laboratory device service information, laboratory device status information, physical laboratory economic data, lean workflow data, and potential improvement data.

30. The system of claim 26, wherein the communication is enabled through a network.

31. The system of claim 30, wherein the network is the Internet.

32. The system of claim 31, wherein the interface component is remote from the display device.

33. The system of claim 31, further comprising a remote access server configured to provide specimen data related to at least one biologic specimen to a location remote from the physical laboratory.

34. The system of claim 33, wherein the specimen data includes at least one of a specimen status and a specimen image.

35. The system of claim 26, wherein the virtual laboratory includes an indication of a workflow through the physical laboratory.

* * * * *